US006197589B1

(12) United States Patent
Maurer et al.

(10) Patent No.: US 6,197,589 B1
(45) Date of Patent: Mar. 6, 2001

(54) ENZYMES FOR DETERGENTS

(75) Inventors: Karl-Heinz Maurer, Erkrath; Albrecht Weiss, Langenfeld, both of (DE); Christian G. Paech, Daly City, CA (US); Dean W. Goddette, Chelmsford, MA (US); Teresa M. Christianson, Petaluma, CA (US); Maria R. Tang, Fairfield, CA (US); Charles Ronald Wilson, Santa Rosa, CA (US)

(73) Assignee: Henkel Kommanditgesellschaft Auf Aktien, Duesseldorf (DE)

( * ) Notice: Subject to any disclaimer, the term of this patent is extended or adjusted under 35 U.S.C. 154(b) by 0 days.

(21) Appl. No.: 09/074,331

(22) Filed: May 7, 1998

Related U.S. Application Data

(62) Division of application No. 08/566,369, filed on Dec. 1, 1995, now Pat. No. 5,801,039, which is a continuation of application No. 08/201,120, filed on Feb. 20, 1994, now abandoned.

(51) Int. Cl.$^7$ ............................ C12N 15/00; C12N 15/57; C12N 15/75; C12N 9/54

(52) U.S. Cl. ..................... 435/471; 435/69.1; 435/221; 435/252.31; 435/320.1; 536/23.2; 536/23.4

(58) Field of Search ............................... 435/221, 252.31, 435/320.1, 468, 476; 536/23.2, 24.1

(56) References Cited

U.S. PATENT DOCUMENTS

| 4,760,025 | 7/1988 | Estell et al. ........................... 510/392 |
|---|---|---|
| 5,340,735 | 8/1994 | Christianson et al. ................ 435/221 |
| 5,352,604 | 10/1994 | Wilson et al. ......................... 435/221 |
| 5,700,676 | * 12/1997 | Bott et al. .............................. 435/221 |
| 5,741,664 | * 4/1998 | Ballinger et al. .................... 435/68.1 |
| 5,780,285 | * 7/1998 | Ballinger et al. ..................... 435/222 |
| 5,801,039 | * 9/1998 | Maurer et al. ........................ 435/221 |
| 5,837,516 | * 11/1998 | Ballinger et al. .................... 435/221 |

FOREIGN PATENT DOCUMENTS

| 0057049 | 8/1982 | (EP) . |
|---|---|---|
| 0130756 | 1/1985 | (EP) . |
| 0247647 | 12/1987 | (EP) . |
| 0260105 | 3/1988 | (EP) . |
| 0328229 | 8/1989 | (EP) . |
| WO 9100345 | 1/1991 | (WO) . |
| WO 9102047 | 2/1991 | (WO) . |
| WO 9102792 | 3/1991 | (WO) . |
| WO 9113678 | 9/1991 | (WO) . |
| WO 9211357 | 7/1992 | (WO) . |
| WO 9302176 | 2/1993 | (WO) . |
| WO 9315180 | 8/1993 | (WO) . |
| WO 9401526 | 1/1994 | (WO) . |

OTHER PUBLICATIONS

Creemers, et al., The Journal of Biological Chemistry, vol. 268, "Modulation of furin–mediated proprotein processing activity by site–directed mutagenesis", pp. 21826–21834, 1993.*

Carter, et al., Proteins: Structure, Function and Genetics, vol. 6. "Engineering subtilisin BPN' for site–specific proteolysis", pp. 240–248, 1989.*

Siezen, et al., FEBS Letters, vol. 234, "Homology modeling of the catalytic domain of human furin, a model for hte eukaryotic subtilisin–like proprotein convertases", pp. 255–266, 1994.*

(List continued on next page.)

*Primary Examiner*—Ponnathapu Achutamurthy
*Assistant Examiner*—William W. Moore
(74) *Attorney, Agent, or Firm*—Wayne C. Jaeschke; Glenn E.J. Murphy; Jeffrey S. Steen

(57) ABSTRACT

This invention relates to proteases with improved application properties in cleaners and detergents. The improvement's achieved by substituting positively charged or uncharged amino acids in the substrate binding region of the wild type subtilisin protease.

63 Claims, 9 Drawing Sheets

OTHER PUBLICATIONS

Smeekens, S. P., et al., Bio/Technology, vol. 11, "Processing of protein precursors by a novel family of subtilisin–related mammalian endoproteases", pp. 182–186, 1993.*

Steiner, et al., The Journal of Biological Chemistry, vol. 267, "The new enzymology of precursor processing proteases", pp. 23435–23438, 1992.*

Rheinnecker, et al., Biochemistry, vol. 32, "Engineering a novel specificity in subtilisin BPN'", pp. 1199–1203, 1993.*

Betzel et al. (1988) Eur. J. Biochem 178, 155–171.
Bott et al. (1988) J. Biol. Chem. 263, 7895–7906.
Godette et al. (1992) J. Mol. Biol. 228, 580–595.
Wells et al. (Aug. 1987) PNAS 84, 5167–5171.
Heinz et al. (1991) J. Mol. Biol. 217, 353–371.
Kraut, J. (1977) Ann. Rev. Biochem. 46, 331–358.
Neidhardt et al. (1988) Protein Eng. 2, 271–276.
Teplyakov et al. (1990) J. Mol. Biol. 214, 261–279.
Estell et al. (1985) J. Biol. 260, 6518–6521.
Matsumura et al. (1989) Proc. Natl. Acad. Sci. USA 86, 6562–6566.
Pantoliano et al. (1988) Biochemistry 27, 8311–8317.
Russell et al. (1987) Nature 328, 496–500.
Siezen et al. (1991) Protein Eng. 4, 719–737.
van Ee, J. J. (1991) Chimicaoggi (7/8), 31–35.
Wells et al. (1988) Trends Biochem. Sci. 13, 291–297.
Russell et al. (1987) J. Mol. Biol. 193, 803–813.
Stanssens et al. (1989) Nucleic Acids Res. 17, 4441–4445.
Ho et al. (1989) Gene 77, 51–59.
Kawamura et al. (1984) J. Bacteriol. 160, 442–444.
Gornall et al. (1948) J. Biol. Chem. 177, 751–766.
Del Mar et al. (1979) Anal. Biochem. 99, 316–320.
Jakobi et al. (1987) Detergents & Textile Washing, VCH, Weinheim, Germany.

* cited by examiner

AvaI
ctcgggacctctttccctgccaggctgaagcggtc
gagccctggagaaagggacggtccgacttcgccag tattcactttcgactgacatttttctaaaac
ataagtatgaagcttgacttgtaaaagatttg agttattaataccaaaaatttaaattggtcct
tcaataattggttttaaatttaaccagga ccaaaaaataggcctaccataattcatttttt
ggttttttatccggatggtatattaagtaaaaa ttctataataattaacagataattggaatagat
aagatattattaattgtcttattaaccttatcta tatattccttctatttaattattctgaataaa
atataataggaagataaattaataagacttattt gaggaggagagtgagtaatgatgaggaaaagagt
ctcctcctcactcattactcctttttctca ttttggcttgggatgctgacggccttcatgctcgt
aaaaccgaccctacgactgccggaagtacgagca
ClaI
gttcacgatggcatcgat
caagtgctaccgtagcta

FIG. 3

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 807 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Bacillus lentus
      (B) STRAIN: DSM 5483

(vii) IMMEDIATE SOURCE:
      (B) CLONE: S3T, R99S, A188P, V193M, V199I (xi) SEQUENCE DESCRIPTION: SEQ ID NO:1:

```
GCGCAAACAG TGCCATGGGG AATTAGCCGT GTGCAAGCCC CGGCTGCCCA TAACCGTGGA        60

TTGACAGGTT CTGGTGTAAA AGTTGCTGTC CTCGATACAG GTATTTCCAC TCATCCAGAC       120

TTAAATATTC GTGGTGGCGC TAGCTTTGTA CCAGGGGAAC CATCCACTCA AGATGGGAAT       180

GGGCATGGCA CGCATGTGGC CGGGACGATT GCTGCTTTAA ACAATTCGAT TGGCGTTCTT       240

GGCGTAGCGC CTAGTGCGGA ACTATACGCT GTTAAAGTTT TAGGAGCCGA CGGTAGCGGT       300

GCAATCAGCT CGATTGCCCA AGGGTTGGAA TGGGCAGGGA ACAATGGCAT GCACGTTGCT       360

AATTTGAGTT TAGGAAGCCC TTCGCCAAGT GCCACACTTG AGCAAGCTGT TAATAGCGCG       420

ACTTCTAGAG GCGTTCTTGT TGTAGCGGCA TCTGGGAATT CAGGTGCAAG CTCAATCAGC       480

TATCCGGCCC GTTATGCGAA CGCAATGGCA GTCGGAGCTA CTGACCAAAA CAACAACCGC       540

GCCAGCTTTT CACAGTATGG CCCAGGGCTT GACATTATGG CACCAGGGGT AAACATTCAG       600
```

```
AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:2:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: S3T, V4I, R99G, A188P, V193M, V199I (xi) SEQUENCE DESCRIPTION: SEQ ID NO:2:

```
GCGCAAACAA TCCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTGGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CCCAGGGCTT GACATTATGG CACCAGGGGT AAACATTCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                          807
```

(2) INFORMATION FOR SEQ ID NO:3:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
    (B) CLONE: S3T, V4I, R99A, A188P, V193M, V199I (xi) SEQUENCE DESCRIPTION: SEQ ID NO:3:

```
GCGCAAACAA TCCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTGCAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACATTCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807
```

(2) INFORMATION FOR SEQ ID NO:4:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: YES (iv) ANTI-SENSE: YES (vi) ORIGINAL SOURCE:
        (A) ORGANISM: Bacillus lentus
        (B) STRAIN: DSM 5483

(vii) IMMEDIATE SOURCE:
        (B) CLONE: S3T, V4I, R99S, A188P, V193M, V199I (xi) SEQUENCE DESCRIPTION: SEQ ID NO:4:

```
GCGCAAACAA TCCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGCGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CCCAGGGCTT GACATTATGG CACCAGGGGT AAACATTCAG     600

AGCACATACC CAGGTTCAAC GTATGCCAGC TTAAACGGTA CATCGATGGC TACTCCTCAT     660
```

```
GTTGCAGGTG CAGCAGCCCT TGTTAAACAA AGAACCCAT CTTGGTCCAA TGTACAAATC        720

CGCAACCATC TAAAGAATAC GGCAACGAGC TTAGGAAGCA CGAACTTGTA TGGAAGCGGA        780

CTTGTCAATG CAGAAGCGGC AACACGC                                           807
```

(2) INFORMATION FOR SEQ ID NO:5:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: S3T, V4I, S154E, A188P, V193M, V199I (xi) SEQUENCE DESCRIPTION: SEQ ID NO:5:

```
GCGCAAACAA TCCCATGGGG AATTAGCCGT GTGCAAGCCC CGGCTGCCCA TAACCGTGGA         60

TTGACAGGTT CTGGTGTAAA AGTTGCTGTC CTCGATACAG GTATTTCCAC TCATCCAGAC        120

TTAAATATTC GTGGTGGCGC TAGCTTTGTA CCAGGGGAAC CATCCACTCA AGATGGGAAT        180

GGGCATGGCA CGCATGTGGC CGGGACGATT GCTGCTTTAA ACAATTCGAT TGGCGTTCTT        240

GGCGTAGCGC CTAGTGCGGA ACTATACGCT GTTAAAGTTT TAGGAGCCGA CGGTAGAGGT        300

GCAATCAGCT CGATTGCCCA AGGGTTGGAA TGGGCAGGGA ACAATGGCAT GCACGTTGCT        360

AATTTGAGTT TAGGAAGCCC TTCGCCAAGT GCCACACTTG AGCAAGCTGT TAATAGCGCG        420

ACTTCTAGAG GCGTTCTTGT TGTAGCGGCA TCTGGGAATG AAGGTGCAAG CTCAATCAGC        480

TATCCGGCCC GTTATGCGAA CGCAATGGCA GTCGGAGCTA CTGACCAAAA CAACAACCGC        540

GCCAGCTTTT CACAGTATGG CCCAGGGCTT GACATTATGG CACCAGGGGT AAACATTCAG        600

AGCACATACC CAGGTTCAAC GTATGCCAGC TTAAACGGTA CATCGATGGC TACTCCTCAT        660

GTTGCAGGTG CAGCAGCCCT TGTTAAACAA AGAACCCAT CTTGGTCCAA TGTACAAATC         720

CGCAACCATC TAAAGAATAC GGCAACGAGC TTAGGAAGCA CGAACTTGTA TGGAAGCGGA        780

CTTGTCAATG CAGAAGCGGC AACACGC                                           807
```

(2) INFORMATION FOR SEQ ID NO:6:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:

(B) CLONE: S3T, V4I, S154D, A188P, V193M, V199I (xi) SEQUENCE DESCRIPTION: SEQ ID NO:6:

```
GCGCAAACAA TCCCATGGGG AATTAGCCGT GTGCAAGCCC CGGCTGCCCA TAACCGTGGA     60
TTGACAGGTT CTGGTGTAAA AGTTGCTGTC CTCGATACAG GTATTTCCAC TCATCCAGAC    120
TTAAATATTC GTGGTGGCGC TAGCTTTGTA CCAGGGGAAC CATCCACTCA AGATGGGAAT    180
GGGCATGGCA CGCATGTGGC CGGGACGATT GCTGCTTTAA ACAATTCGAT TGGCGTTCTT    240
GGCGTAGCGC CTAGTGCGGA ACTATACGCT GTTAAAGTTT AGGAGCCGA CGGTAGAGGT     300
GCAATCAGCT CGATTGCCCA AGGGTTGGAA TGGGCAGGGA ACAATGGCAT GCACGTTGCT    360
AATTTGAGTT TAGGAAGCCC TTCGCCAAGT GCCACACTTG AGCAAGCTGT TAATAGCGCG    420
ACTTCTAGAG GCGTTCTTGT TGTAGCGGCA TCTGGGAATG ACGGTGCAAG CTCAATCAGC    480
TATCCGGCCC GTTATGCGAA CGCAATGGCA GTCGGAGCTA CTGACCAAAA CAACAACCGC    540
GCCAGCTTTT CACAGTATGG CCCAGGGCTT GACATTATGG CACCAGGGGT AAACATTCAG    600
AGCACATACC CAGGTTCAAC GTATGCCAGC TTAAACGGTA CATCGATGGC TACTCCTCAT    660
GTTGCAGGTG CAGCAGCCCT TGTTAAACAA AAGAACCCAT CTTGGTCCAA TGTACAAATC    720
CGCAACCATC TAAAGAATAC GGCAACGAGC TTAGGAAGCA CGAACTTGTA TGGAAGCGGA    780
CTTGTCAATG CAGAAGCGGC AACACGC                                        807
```

(2) INFORMATION FOR SEQ ID NO:7:

(i) SEQUENCE CHARACTERISTICS:
(A) LENGTH: 807 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bacillus lentus
(B) STRAIN: DSM 5483

(vii) IMMEDIATE SOURCE:
(B) CLONE: S3T, V4I, A188P, V193M, V199I, L211D (xi) SEQUENCE DESCRIPTION: SEQ ID NO:7:

```
GCGCAAACAA TCCCATGGGG AATTAGCCGT GTGCAAGCCC CGGCTGCCCA TAACCGTGGA     60
TTGACAGGTT CTGGTGTAAA AGTTGCTGTC CTCGATACAG GTATTTCCAC TCATCCAGAC    120
TTAAATATTC GTGGTGGCGC TAGCTTTGTA CCAGGGGAAC CATCCACTCA AGATGGGAAT    180
GGGCATGGCA CGCATGTGGC CGGGACGATT GCTGCTTTAA ACAATTCGAT TGGCGTTCTT    240
GGCGTAGCGC CTAGTGCGGA ACTATACGCT GTTAAAGTTT AGGAGCCGA CGGTAGAGGT     300
GCAATCAGCT CGATTGCCCA AGGGTTGGAA TGGGCAGGGA ACAATGGCAT GCACGTTGCT    360
AATTTGAGTT TAGGAAGCCC TTCGCCAAGT GCCACACTTG AGCAAGCTGT TAATAGCGCG    420
ACTTCTAGAG GCGTTCTTGT TGTAGCGGCA TCTGGGAATT CAGGTGCAAG CTCAATCAGC    480
TATCCGGCCC GTTATGCGAA CGCAATGGCA GTCGGAGCTA CTGACCAAAA CAACAACCGC    540
GCCAGCTTTT CACAGTATGG CCCAGGGCTT GACATTATGG CACCAGGGGT AAACATTCAG    600
AGCACATACC CAGGTTCAAC GTATGCCAGC GACAACGGTA CATCGATGGC TACTCCTCAT    660
GTTGCAGGTG CAGCAGCCCT TGTTAAACAA AAGAACCCAT CTTGGTCCAA TGTACAAATC    720
```

CGCAACCATC TAAAGAATAC GGCAACGAGC TTAGGAAGCA CGAACTTGTA TGGAAGCGGA        780

CTTGTCAATG CAGAAGCGGC AACACGC                                          807

(2) INFORMATION FOR SEQ ID NO:8:

(i) SEQUENCE CHARACTERISTICS:
       (A) LENGTH: 807 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Bacillus lentus
       (B) STRAIN: DSM 5483

(vii) IMMEDIATE SOURCE:
       (B) CLONE: S3T, V4I, R99G, A188P, V193M, V199I, L211D (xi) SEQUENCE DESCRIPTION: SEQ ID NO:8:

GCGCAAACAA TCCCATGGGG AATTAGCCGT GTGCAAGCCC CGGCTGCCCA TAACCGTGGA         60

TTGACAGGTT CTGGTGTAAA AGTTGCTGTC CTCGATACAG GTATTTCCAC TCATCCAGAC        120

TTAAATATTC GTGGTGGCGC TAGCTTTGTA CCAGGGGAAC CATCCACTCA AGATGGGAAT        180

GGGCATGGCA CGCATGTGGC CGGGACGATT GCTGCTTTAA ACAATTCGAT TGGCGTTCTT        240

GGCGTAGCGC CTAGTGCGGA ACTATACGCT GTTAAAGTTT TAGGAGCCGA CGGTGGAGGT        300

GCAATCAGCT CGATTGCCCA AGGGTTGGAA TGGGCAGGGA ACAATGGCAT GCACGTTGCT        360

AATTTGAGTT TAGGAAGCCC TTCGCCAAGT GCCACACTTG AGCAAGCTGT TAATAGCGCG        420

ACTTCTAGAG GCGTTCTTGT TGTAGCGGCA TCTGGGAATT CAGGTGCAAG CTCAATCAGC        480

TATCCGGCCC GTTATGCGAA CGCAATGGCA GTCGGAGCTA CTGACCAAAA CAACAACCGC        540

GCCAGCTTTT CACAGTATGG CCCAGGGCTT GACATTATGG CACCAGGGGT AAACATTCAG        600

AGCACATACC CAGGTTCAAC GTATGCCAGC GACAACGGTA CATCGATGGC TACTCCTCAT        660

GTTGCAGGTG CAGCAGCCCT TGTTAAACAA AAGAACCCAT CTTGGTCCAA TGTACAAATC        720

CGCAACCATC TAAAGAATAC GGCAACGAGC TTAGGAAGCA CGAACTTGTA TGGAAGCGGA        780

CTTGTCAATG CAGAAGCGGC AACACGC                                          807

(2) INFORMATION FOR SEQ ID NO:9:

(i) SEQUENCE CHARACTERISTICS:
       (A) LENGTH: 807 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Bacillus lentus
       (B) STRAIN: DSM 5483

(vii) IMMEDIATE SOURCE:
       (B) CLONE: S3T, V4I, S154E, A188P, V193M, V199I, L211D (xi) SEQUENCE DESCRIPTION: SEQ ID NO:9:

```
GCGCAAACAA TCCCATGGGG AATTAGCCGT GTGCAAGCCC CGGCTGCCCA TAACCGTGGA      60
TTGACAGGTT CTGGTGTAAA AGTTGCTGTC CTCGATACAG GTATTTCCAC TCATCCAGAC     120
TTAAATATTC GTGGTGGCGC TAGCTTTGTA CCAGGGGAAC CATCCACTCA AGATGGGAAT     180
GGGCATGGCA CGCATGTGGC CGGGACGATT GCTGCTTTAA ACAATTCGAT TGGCGTTCTT     240
GGCGTAGCGC CTAGTGCGGA ACTATACGCT GTTAAAGTTT TAGGAGCCGA CGGTAGAGGT     300
GCAATCAGCT CGATTGCCCA AGGGTTGGAA TGGGCAGGGA ACAATGGCAT GCACGTTGCT     360
AATTTGAGTT TAGGAAGCCC TTCGCCAAGT GCCACACTTG AGCAAGCTGT TAATAGCGCG     420
ACTTCTAGAG GCGTTCTTGT TGTAGCGGCA TCTGGGAATG AAGGTGCAAG CTCAATCAGC     480
TATCCGGCCC GTTATGCGAA CGCAATGGCA GTCGGAGCTA CTGACCAAAA CAACAACCGC     540
GCCAGCTTTT CACAGTATGG CCCAGGGCTT GACATTATGG CACCAGGGGT AAACATTCAG     600
AGCACATACC CAGGTTCAAC GTATGCCAGC GACAACGGTA CATCGATGGC TACTCCTCAT     660
GTTGCAGGTG CAGCAGCCCT TGTTAAACAA AAGAACCCAT CTTGGTCCAA TGTACAAATC     720
CGCAACCATC TAAAGAATAC GGCAACGAGC TTAGGAAGCA CGAACTTGTA TGGAAGCGGA     780
CTTGTCAATG CAGAAGCGGC AACACGC                                         807
```

(2) INFORMATION FOR SEQ ID NO:10:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F11

(xi) SEQUENCE DESCRIPTION: SEQ ID NO:10:

```
Ala Gln Thr Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ser Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
```

```
              130                 135                 140
Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:11:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F43

(xi) SEQUENCE DESCRIPTION: SEQ ID NO:11:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Gly Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Ser Ser Ile Ser
145                 150                 155                 160
```

```
Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

(2) INFORMATION FOR SEQ ID NO:12:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F44

(xi) SEQUENCE DESCRIPTION: SEQ ID NO:12:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ala Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175
```

```
Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:13:

(i) SEQUENCE CHARACTERISTICS:
          (A) LENGTH: 269 amino acids
          (B) TYPE: amino acid
          (C) STRANDEDNESS:
          (D) TOPOLOGY: unknown (ii) MOLECULE TYPE: peptide (iii) HYPOTHETICAL: NO (iv) ANTI-SENSE: NO (vi) ORIGINAL SOURCE:
          (A) ORGANISM: Bacillus lentus
          (B) STRAIN: DSM 5483

(vii) IMMEDIATE SOURCE:
          (B) CLONE: F45

(xi) SEQUENCE DESCRIPTION: SEQ ID NO:13:

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Ser Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
```

```
               195                 200                 205
Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265

(2) INFORMATION FOR SEQ ID NO:14:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F46

(xi) SEQUENCE DESCRIPTION: SEQ ID NO:14:

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
                35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Glu Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
                180                 185                 190

Met Ala Pro Gly Val Asn Ile Gln Ser Thr Tyr Pro Gly Ser Thr Tyr
                195                 200                 205

Ala Ser Leu Asn Gly Thr Ser Met Ala Thr Pro His Val Ala Gly Ala
        210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:15:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F47

(xi) SEQUENCE DESCRIPTION: SEQ ID NO:15:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
130                 135                 140

Val Leu Val Val Ala Ala Ser Gly Asn Asp Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240
```

```
Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

(2) INFORMATION FOR SEQ ID NO:16:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: F49

(xi) SEQUENCE DESCRIPTION: SEQ ID NO:16:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
            195                 200                 205

Ala Ser Asp Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
            245                 250                 255

Tyr Gly Ser Gly Leu Val Asn Ala Glu Ala Ala Thr Arg
            260                 265
```

-continued 260            265

(2) INFORMATION FOR SEQ ID NO:17:

(i) SEQUENCE CHARACTERISTICS:
       (A) LENGTH: 269 amino acids
       (B) TYPE: amino acid
       (C) STRANDEDNESS:
       (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
         (B) CLONE: F54

(xi) SEQUENCE DESCRIPTION: SEQ ID NO:17:

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Gly Gly Ala Ile Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Asp Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:18:

(i) SEQUENCE CHARACTERISTICS:
            (A) LENGTH: 269 amino acids
            (B) TYPE: amino acid
            (C) STRANDEDNESS:
            (D) TOPOLOGY: unknown (ii) MOLECULE TYPE: peptide (iii) HYPOTHETICAL: NO (iv) ANTI-SENSE: NO (vi) ORIGINAL SOURCE:
            (A) ORGANISM: Bacillus lentus
            (B) STRAIN: DSM 5483

(vii) IMMEDIATE SOURCE:
            (B) CLONE: F55

(xi) SEQUENCE DESCRIPTION: SEQ ID NO:18:

Ala Gln Thr Ile Pro Trp Gly Ile Ser Arg Val Gln Ala Pro Ala Ala
1               5                  10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Glu Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Asp Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:19:

(i) SEQUENCE CHARACTERISTICS:
            (A) LENGTH: 807 base pairs
            (B) TYPE: nucleic acid (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus lentus
            (B) STRAIN: DSM 5483

(vii) IMMEDIATE SOURCE:
            (B) CLONE: wild type (ix) FEATURE:
            (A) NAME/KEY: mutation
            (B) LOCATION: one-of (300, 266, 807, 678, 789, 789)
                one-of (789, 789, 567, 678)
            (D) OTHER INFORMATION: /product= "mutation site"

(xi) SEQUENCE DESCRIPTION: SEQ ID NO:19:

```
GCGCAATCAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120

TTAAATATTC GTGGTGGCGC TAGCTTTGTA CCAGGGGAAC CATCCACTCA AGATGGGAAT     180

GGGCATGGCA CGCATGTGGC CGGGACGATT GCTGCTTTAA ACAATTCGAT TGGCGTTCTT     240

GGCGTAGCGC CTAGTGCGGA ACTATACGCT GTTAAAGTTT TAGGAGCCGA CGGTAGAGGT     300

GCAATCAGCT CGATTGCCCA AGGGTTGGAA TGGGCAGGGA ACAATGGCAT GCACGTTGCT     360

AATTTGAGTT TAGGAAGCCC TTCGCCAAGT GCCACACTTG AGCAAGCTGT TAATAGCGCG     420

ACTTCTAGAG GCGTTCTTGT TGTAGCGGCA TCTGGGAATT CAGGTGCAAG CTCAATCAGC     480

TATCCGGCCC GTTATGCGAA CGCAATGGCA GTCGGAGCTA CTGACCAAAA CAACAACCGC     540

GCCAGCTTTT CACAGTATGG CGCAGGGCTT GACATTGTCG CACCAGGGGT AAACGTGCAG     600

AGCACATACC CAGGTTCAAC GTATGCCAGC TTAAACGGTA CATCGATGGC TACTCCTCAT     660

GTTGCAGGTG CAGCAGCCCT TGTTAAACAA AAGAACCCAT CTTGGTCCAA TGTACAAATC     720

CGCAACCATC TAAAGAATAC GGCAACGAGC TTAGGAAGCA CGAACTTGTA TGGAAGCGGA     780

CTTGTCAATG CAGAAGCGGC AACACGC                                        807
```

(2) INFORMATION FOR SEQ ID NO:20:

(i) SEQUENCE CHARACTERISTICS:
            (A) LENGTH: 807 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Bacillus lentus
            (B) STRAIN: DSM 5483

(vii) IMMEDIATE SOURCE:
            (B) CLONE: S3T, A188P, V193M, V199I (xi) SEQUENCE DESCRIPTION: SEQ ID NO:20:

```
GCGCAAACAG TGCCATGGGG AATTAGCCGT GTGCAAGCCC CGGCTGCCCA TAACCGTGGA      60

TTGACAGGTT CTGGTGTAAA AGTTGCTGTC CTCGATACAG GTATTTCCAC TCATCCAGAC     120
```

```
TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CCCAGGGCTT GACATTATGG CACCAGGGGT AAACATTCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:21:

(i) SEQUENCE CHARACTERISTICS:
        (A) LENGTH: 807 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bacillus lentus
        (B) STRAIN: DSM 5483

(vii) IMMEDIATE SOURCE:
        (B) CLONE: S3T, V4I, A188P, V193M, V199I (xi) SEQUENCE DESCRIPTION: SEQ ID NO:21:

```
GCGCAAACAA TCCCATGGGG AATTAGCCGT GTGCAAGCCC CGGCTGCCCA TAACCGTGGA       60

TTGACAGGTT CTGGTGTAAA AGTTGCTGTC CTCGATACAG GTATTTCCAC TCATCCAGAC      120

TTAAATATTC GTGGTGGCGC TAGCTTTGTA CCAGGGGAAC CATCCACTCA AGATGGGAAT      180

GGGCATGGCA CGCATGTGGC CGGGACGATT GCTGCTTTAA ACAATTCGAT TGGCGTTCTT      240

GGCGTAGCGC CTAGTGCGGA ACTATACGCT GTTAAAGTTT TAGGAGCCGA CGGTAGAGGT      300

GCAATCAGCT CGATTGCCCA AGGGTTGGAA TGGGCAGGGA ACAATGGCAT GCACGTTGCT      360

AATTTGAGTT TAGGAAGCCC TTCGCCAAGT GCCACACTTG AGCAAGCTGT TAATAGCGCG      420

ACTTCTAGAG GCGTTCTTGT TGTAGCGGCA TCTGGGAATT CAGGTGCAAG CTCAATCAGC      480

TATCCGGCCC GTTATGCGAA CGCAATGGCA GTCGGAGCTA CTGACCAAAA CAACAACCGC      540

GCCAGCTTTT CACAGTATGG CCCAGGGCTT GACATTATGG CACCAGGGGT AAACATTCAG      600

AGCACATACC CAGGTTCAAC GTATGCCAGC TTAAACGGTA CATCGATGGC TACTCCTCAT      660

GTTGCAGGTG CAGCAGCCCT TGTTAAACAA AAGAACCCAT CTTGGTCCAA TGTACAAATC      720

CGCAACCATC TAAAGAATAC GGCAACGAGC TTAGGAAGCA CGAACTTGTA TGGAAGCGGA      780

CTTGTCAATG CAGAAGCGGC AACACGC                                         807
```

(2) INFORMATION FOR SEQ ID NO:22:

(i) SEQUENCE CHARACTERISTICS:
    (A) LENGTH: 269 amino acids
    (B) TYPE: amino acid
    (C) STRANDEDNESS:
    (D) TOPOLOGY: unknown (ii) MOLECULE TYPE: peptide (iii) HYPOTHETICAL: NO (iv) ANTI-SENSE: NO (vi) ORIGINAL SOURCE:
    (A) ORGANISM: Bacillus lentus
    (B) STRAIN: DSM 5843

(vii) IMMEDIATE SOURCE:
    (B) CLONE: BLAP (xi) SEQUENCE DESCRIPTION: SEQ ID NO:22:

```
Ala Gln Ser Val Pro Trp Gly Ile Ser Arg Val Gln Ala Pro Ala Ala
1               5                   10                  15
His Asn Arg Gly Leu Thr Gly Ser Gly Val Lys Val Ala Val Leu Asp
            20                  25                  30
Thr Gly Ile Ser Thr His Pro Asp Leu Asn Ile Arg Gly Gly Ala Ser
        35                  40                  45
Phe Val Pro Gly Glu Pro Ser Thr Gln Asp Gly Asn Gly His Gly Thr
50                  55                  60
His Val Ala Gly Thr Ile Ala Ala Leu Asn Asn Ser Ile Gly Val Leu
65                  70                  75                  80
Gly Val Ala Pro Ser Ala Glu Leu Tyr Ala Val Lys Val Leu Gly Ala
                85                  90                  95
Asp Gly Arg Gly Ala Ile Ser Ser Ile Ala Gln Gly Leu Glu Trp Ala
            100                 105                 110
Gly Asn Asn Gly Met His Val Ala Asn Leu Ser Leu Gly Ser Pro Ser
        115                 120                 125
Pro Ser Ala Thr Leu Glu Gln Ala Val Asn Ser Ala Thr Ser Arg Gly
130                 135                 140
Val Leu Val Val Ala Ala Ser Gly Asn Ser Gly Ala Ser Ser Ile Ser
145                 150                 155                 160
Tyr Pro Ala Arg Tyr Ala Asn Ala Met Ala Val Gly Ala Thr Asp Gln
                165                 170                 175
Asn Asn Asn Arg Ala Ser Phe Ser Gln Tyr Gly Ala Gly Leu Asp Ile
            180                 185                 190
Val Ala Pro Gly Val Asn Val Gln Ser Thr Tyr Pro Gly Ser Thr Tyr
        195                 200                 205
Ala Ser Leu Asn Gly Thr Ser Met Ala Thr Pro His Val Ala Gly Ala
210                 215                 220
Ala Ala Leu Val Lys Gln Lys Asn Pro Ser Trp Ser Asn Val Gln Ile
225                 230                 235                 240
Arg Asn His Leu Lys Asn Thr Ala Thr Ser Leu Gly Ser Thr Asn Leu
                245                 250                 255
Tyr Gly Ser Gly Leu Val Asn Ala Glu Ala Ala Thr Arg
            260                 265
```

(2) INFORMATION FOR SEQ ID NO:23:

(i) SEQUENCE CHARACTERISTICS:
        (A) LENGTH: 269 amino acids
        (B) TYPE: amino acid (C) STRANDEDNESS:
        (D) TOPOLOGY: unknown (ii) MOLECULE TYPE: peptide (iii) HYPOTHETICAL: NO (iv) ANTI-SENSE: NO (vi) ORIGINAL SOURCE:
        (A) ORGANISM: Bacillus lentus
        (B) STRAIN: DSM 5843

(vii) IMMEDIATE SOURCE:
        (B) CLONE: M130

(xi) SEQUENCE DESCRIPTION: SEQ ID NO:23:

Ala Gln Thr Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

(2) INFORMATION FOR SEQ ID NO:24:

(i) SEQUENCE CHARACTERISTICS:
        (A) LENGTH: 269 amino acids
        (B) TYPE: amino acid
        (C) STRANDEDNESS:
        (D) TOPOLOGY: unknown (ii) MOLECULE TYPE: peptide -continued (iii) HYPOTHETICAL: NO (iv) ANTI-SENSE: NO (vi) ORIGINAL SOURCE:
(A) ORGANISM: Bacillus lentus
(B) STRAIN: DSM 5843

(vii) IMMEDIATE SOURCE:
(B) CLONE: M131

(xi) SEQUENCE DESCRIPTION: SEQ ID NO:24:

```
Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Pro Gly Leu Asp Ile
            180                 185                 190

Met Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

ENZYMES FOR DETERGENTS

This is a divisional of prior application Ser. No. 08/566,369 filed Dec. 1, 1995, now U.S. Pat. No. 5,801,039, which was a continuation of prior application Ser. No. 08/201,120, filed Feb. 20, 1994, now abandoned.

BACKGROUND OF THE INVENTION

1. Field of the Invention

This invention relates to novel mutant proteolytic enzymes with improved properties relative to the wild type enzyme in cleaning and detergent formulations, to nucleotide sequences encoding the improved proteases, and to host organisms containing the nucleotide sequences encoding the novel proteases. This invention also includes within its scope new and improved detergent and cleansing compositions containing an effective cleansing amount of said enzymes.

2. Description of the Related Art

Subtilisins are a family of bacterial extracellular proteases with molecular masses of 20,000 to 45,000 daltons produced by a soil bacillus e.g. *Bacillus amyloliquefaciens*. Proteases are enzymes which catalyze the hydrolysis of peptide linkages in protein and peptide substrates and of ester bonds in some terminal esters. Subtilisins belong to the group of serine proteases which initiate the nucleophilic attack on the peptide (ester) bond by a serine residue at the active site. Subtilisins are physically and chemically well characterized enzymes.

The three-dimensional structure of several subtilisins has been elucidated in detail by X-ray diffraction studies (Betzel, C., Pal, G. P., and Saenger, W. (1988) Eur. J. Biochem. 178, 155–171; Bott, R., Ultsch, M., Kossiakoff, A., Graycar, T., Katz, B., and Power, S. (1988) J. Biol. Chem. 263, 7895–7906; Goddette, D. W., Paech, C., Yang, S. S., Mielenz, J. R., Bystroff, C., Wilke, M., and Fletterick, R. J. (1992) J. Mol. Biol. 228, 580–595; Heinz, D. W., Priestle, J. P., Rahuel, J., Wilson, K. S., and Grütter, M. G. (1991) J. Mol. Biol. 217, 353–371; Kraut, J. (1977) Annu. Rev. Biochem. 46, 331–358; Neidhart, D. J. and Petsko, G. A. (1988) Protein Eng. 2, 271–276; Teplyakov, A. V., Kuranova, I. P., Harutyunyan, E. H., Vainshtein, B. K., Frbömmel, C., Höhne, W.-E., and Wilson, K. S. (1990) J. Mol. Biol. 214, 261–279). In spite of this wealth of information the structure/function differences between these closely related subtilisins have not been explained.

Subtilisins are widely used in commercial products (for example, in laundry and dish washing detergents, contact lens cleaners) and for research purposes (catalysts in synthetic organic chemistry). One member of the subtilisin family, a highly alkaline protease for use in detergent formulations has been described in patent application WO 91/02792. This *Bacillus lentus* alkaline protease (BLAP) can be obtained in commercial quantities from *Bacillus licheniformis* ATCC 53926 strain transformed by an expression plasmid harboring the wild type BLAP gene under the control of the *B. licheniformis* ATCC 53926 alkaline protease gene promoter. The crystal structure of BLAP has been deduced (Goddette, D. W., et al. (1992) J. Mol. Biol. 228, 580–595; WO 92/21760), and the coordinates have been deposited with the Brookhaven Protein Data Bank.

Unless other wise noted the numbering of the amino acid positions is according to the sequence in BLAP (269 amino acids), which differs from that of subtilisin BPN' (275 amino acids). When aligned for optimal sequence homology the following pattern emerges. In BLAP positions 1 to 35, 36 to 54, 55 to 160, and 161 to 269 correspond to positions 1 to 35, 37 to 55, 57 to 162, and 167 to 275, respectively, in subtilisin BPN'.

In order to describe protease variants according to the invention, the following nomenclature is used: [Original Amino Acid; Position from N-terminus of the mature enzyme; Substituted Amino Acid]. For example, the substitution of valine with isoleucine at position 4 in BLAP is designated as V4I. The list of abbreviations for amino acids is shown in Table 1.

TABLE 1

| Amino Acid Nomenclature |
|---|
| A = Ala = Alanine |
| C = Cys = Cysteine |
| D = Asp = Aspartic acid |
| E = Glu = Glutamic acid |
| F = Phe = Phenylalanine |
| G = Gly = Glycine |
| H = His = Histidine |
| I = Ile = Isoleucine |
| K = Lys = Lysine |
| L = Leu = Leucine |
| M = Met = Methionine |
| N = Asn = Asparagine |
| P = Pro = Proline |
| Q = Gln = Glutamine |
| R = Arg = Arginine |
| S = Ser = Serine |
| T = Thr = Threonine |
| V = Val = Valine |
| W = Trp = Tryptophan |
| Y = Tyr = Tyrosine |

Multiple mutations within the same protein molecule are indicated as the sum of individual mutations, i.e. S3T+V4I+A188P+V193M+V199I.

Protection against thermal and chemical inactivation and improvement of washing and cleaning performance are primary objectives in research and development of proteases for technical as well as for commercial applications. A large number of enzymes including subtilisins have been generated by random and site-specific mutagenesis and they provide some guidelines for a rational approach to the improvement of thermal and chemical stability (Estell, D. A., Graycar, T. P., and Wells, J. A. (1985) J. Biol. Chem. 260, 6518–6521; Matsumura, M., Becktel, W. J., Levitt, M., and Matthews, B. W. (1989) Proc. Natl. Acad. Sci. USA 86, 6562–6566; Pantoliano, M. W., Whitlow, M., Wood, J. F., Rollence, M. L., Finzel, B. C., Gilliland, G. L., Poulos, T. L., and Bryan, P. N. (1988) Biochemistry 27, 8311–8317; Russell, A. J. and Fersht, A. R. (1987) Nature 328, 496–500; Siezen, R. J., De Vos, W. M., Leunissen, J. A. M., and Dijkstra, B. W. (1991) Protein Eng. 4, 719–737; van Ee, J. H. (1991) Chimicaoggi (7/8), 31–35; Wells, J. A. and Estell, D. A. (1988) Trends Biochem. Sci. 13, 291–297). The modulation of enzymic activity, in particular rate enhancement or optimization for a subset of substrates, is a far more complex problem. EP 0260105 teaches the construction of subtilisin BPN' mutants with altered transesterification rate/hydrolysis rate ratios and nucleophile specificities by changing specific amino acid residues within 15 Å of the catalytic triad. Russell, A. J., and Fersht, A. R. (1987) J. Mol. Biol. 193: 803–813, teach the isolation of a subtilisin BPN' mutant (D099S) that had a change in the surface charge 14 to 15 Å from the active site. This substitution causes an effect on the pH dependence of the subtilisin's catalytic reaction. Neither of these publications teach how to predict amino acid alterations that will improve the wash performance of the protease. EP 0130756, EP 0247647, and U.S. Pat. No. 4,760,025 teach a saturation mutation method where one or multiple mutations are introduced into the subtilisin BPN' at amino acid residues (BPN' numbering) Asp32, Asn155, Tyr104, Met222, Gly166, His64, Ser221, Gly169, Glu156, Ser33, Phe189, Tyr217, and/or Ala152. Using this approach mutant proteases exhibiting improved oxidative stability, altered substrate specificity, and/or altered pH activity are obtained. These publications also teach that mutations within the active site region of the protease are the most likely to influence activity. However, neither EP0130756, EP 0247647, nor U.S. Pat. No. 4,760,025 teach a method for predicting amino acid alterations that will improve the wash performance of the protease.

Most of the information on the catalytic activity of subtilisins has been collected by examining the hydrolysis of small, well defined peptide substrates. Yet, little is known about interactions with large protein substrates. This is especially true for the wash performance of proteases where the substrate is attached to a textile surface and catalysis takes place in presence of interfering compounds such as bleach, tensides, and builders.

EP 0328229 teaches the isolation and characterization of PB92 subtilisin mutants with improved properties for laundry detergent applications based upon wash test results. It teaches that biochemical properties are not reliable parameters for predicting enzyme performance in the wash. Methods for selection of mutations involve the substitution of amino acids by other amino acids in the same category (polar, nonpolar, aromatic, charged, aliphatic, and neutral), the substitution of polar amino acids asparagine and glutamine by charged amino acids, and increasing the anionic character of the protease at sites not involved with the active site. No method for identifying which specific amino acids should be altered is taught. Patent application WO 91/00345 (Novo-Nordisk) teaches a method to improve the wash performance of a subtilisin by the modification of the isoelectric point of subtilisin Carlsberg and subtilisin 309 to match the pH of the washing solution, where the enzyme is supposed to be used. However, since the highly alkaline subtilisins have pI values close to the pH of detergents under European washing conditions, this approach offers no obvious advantage. WO 91/00345 also teaches that changes in amino acids more than 15 Å from the catalytic triad can result in changes in the kinetic properties of the enzyme. A total of 116 different amino acids out of a total of 269 amino acids present in subtilisin 309 are suggested as possible sites for substitution, addition or deletion to modify the net electric charge of the enzyme.

Patent application WO 92/11357 (Novo-Nordisk) teaches increased pH-stability and improved washability of subtilisins by reduction of pH-dependent charges of the molecule. This means the introduction of mutations to approach substantial constancy of charge over a pH range.

Preferably, an almost zero net charge change in the pH range from 7 to 11. European patent application No. 0 57 049 A1 discloses certain mutant proteolytic enzymes. These enzymes are said to have at least 70% homology with the amino acid sequence of PB92 serine protease and differ by at least one amino acid corresponding to 99, 102, 116, 126, 127, 128, 130, 160, 203, 211, and 212 in the PB92 serine protease. The mutant protease is prepared by growing a microorganism host strain transformed with an expression vector comprising a DNA sequence and encoding a mutant protease to produce the designed mutant protease.

SUMMARY OF THE INVENTION

The wild-type protease from which the mutant proteases according to the invention are derived is a *Bacillus lentus* alkaline protease (BLAP) obtained from DSM 5483 having 269 amino acid residues, a molecular mass of 26,823 daltons and a calculated isoelectric point of 9.7 based on standard pK values. The BLAP gene is obtained by isolating the chromosomal DNA from the *B. lentus* strain DSM 5483, constructing DNA probes having homology to putative DNA sequences encoding regions of the *B. lentus* protease, preparing genomic libraries from the isolated chromosomal DNA and screening the libraries for the gene of interest by hybridization to the probes.

Mutants of *B. lentus* DSM 5483 protease with improved thermal and surfactant stability have been described in patent application Ser. No. 07/706,691 filed May 29, 1991. In general the mutations described in this invention are introduced into wild-type BLAP with the following amino acid replacements: S3T, V4I, A188P, V193M, and V199I (numbering according to the BLAP sequence).

Research directed towards the binding of the protease to the high molecular protein substrate on the textile revealed the importance of the charged amino acids situated in the proximity of the substrate binding site. It could be shown that the removal of positively charged amino acid residues or the introduction of negatively charged amino acid residues in the region of the substrate binding pocket of the protease leads towards better wash performance compared to the wild type.

BRIEF DESCRIPTION OF THE FIGURES

FIG. 3 shows the DNA sequence for the AvaI/ClaI fragment from the N-terminal region of the ATCC 53926 alkaline protease gene discussed in Example 2. The fragment includes the putative promoter, ribosomal binding site, initiation codon, and most of the pre sequence. The 292 base pair fragment is flanked by AvaI and ClaI restriction sites at its 5' and 3' ends, respectively.

The plasmid still encodes resistance to chloramphenicol ($Cm^R$)

Figure 5:
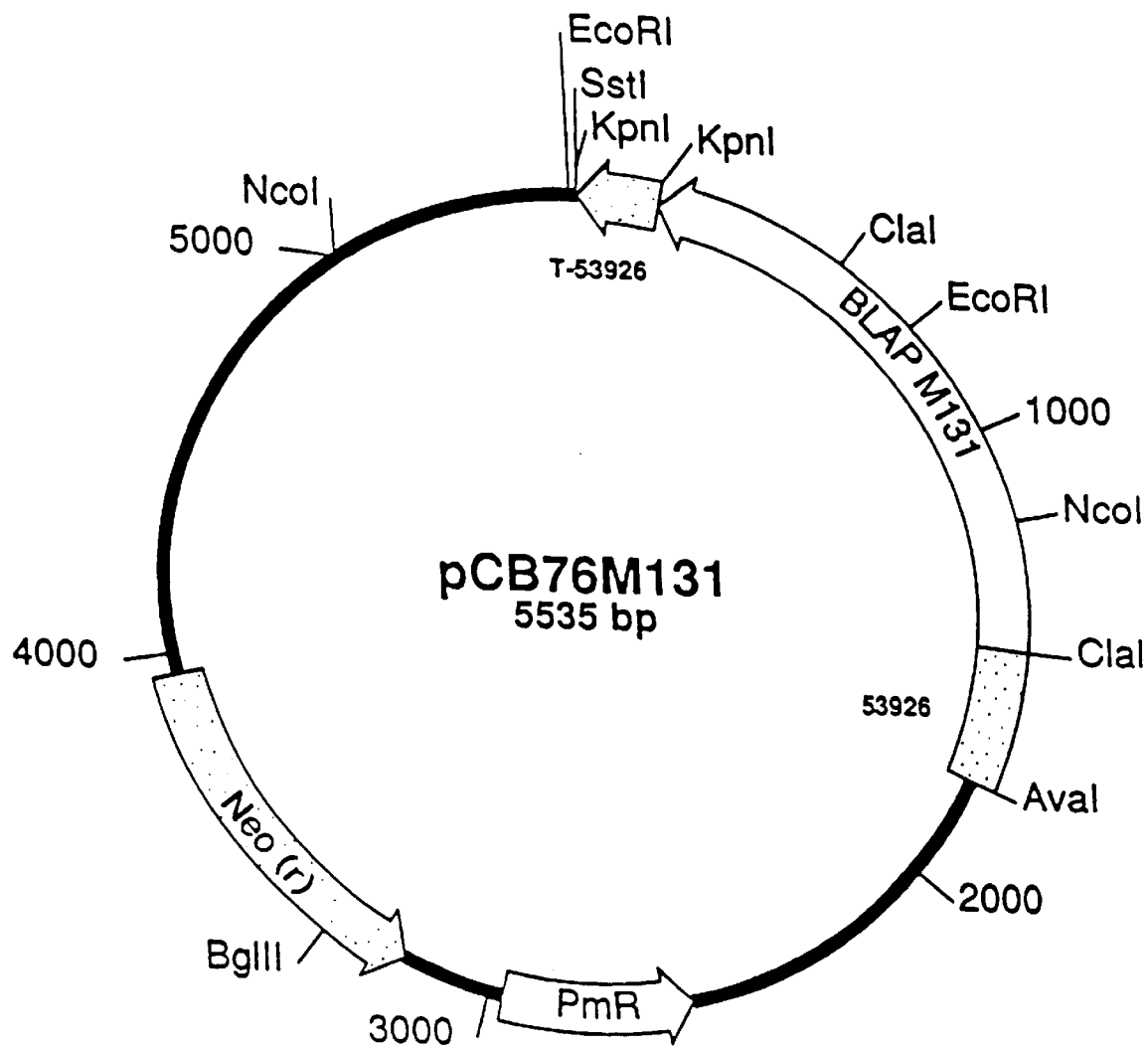

FIG. 5 shows the restriction map for Bacillus plasmid pCB76M131 which contains the gene encoding BLAP variant M131. Included is the hybrid fusion between the ATCC 53926 protease and BLAP as described for pCB13C in FIG. 2. Also presence is the transcription terminator sequence from the 53926 alkaline protease gene. This is a pUB110 based plasmid which encodes resistance to kanamycin.

Figure 6:
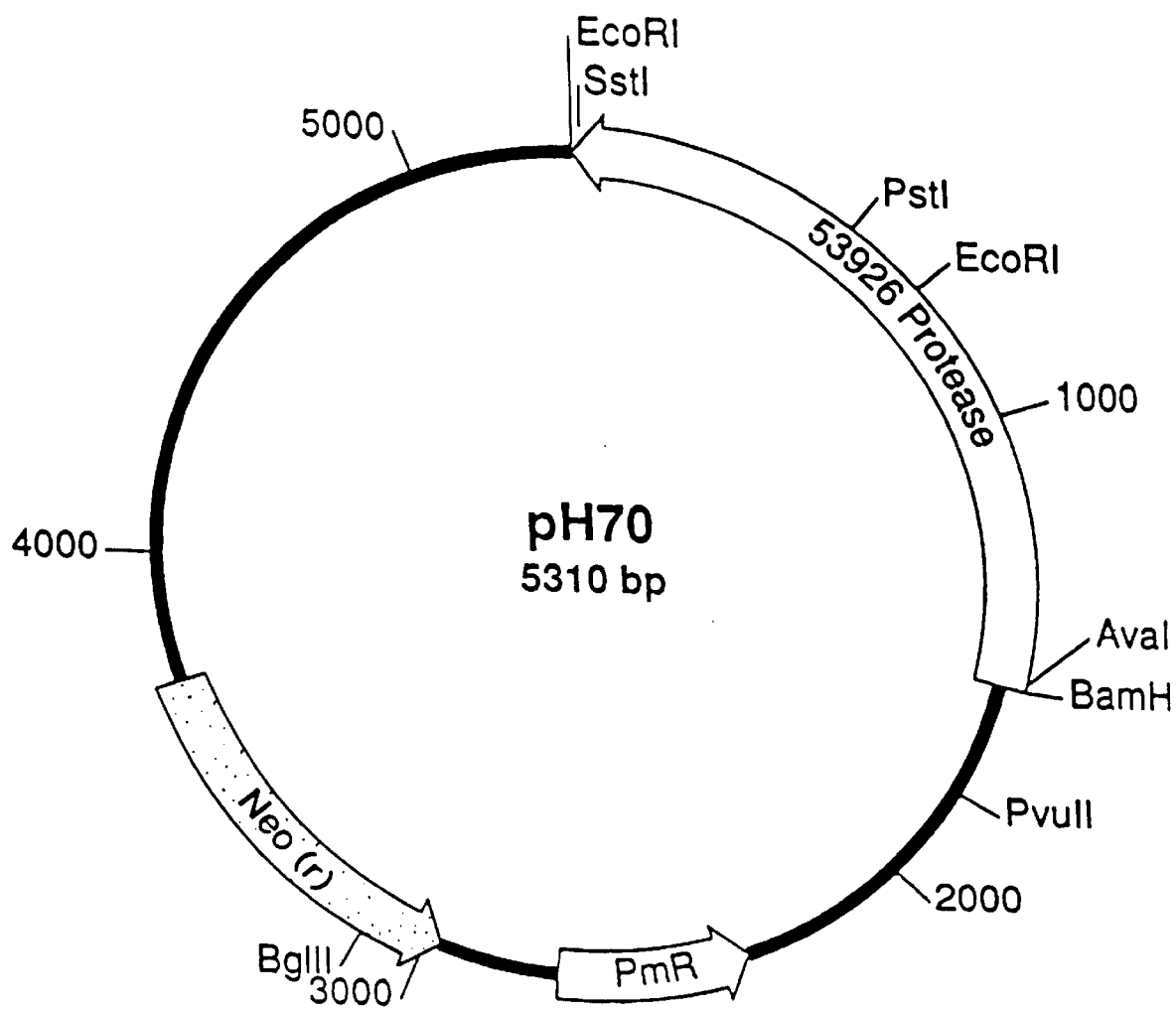

FIG. 6 shows a restriction map for Bacillus plasmid pH70 which is a derivative of plasmid pUB110 containing the ATCC 53926 alkaline protease gene. An EcoRI/BamHI fragment carrying the protease gene was cloned between the EcoRI and BamHI sites on pUB110. This plasmid is discussed in Example 3: Cloning of mutant protease genes. Plasmid pH70 encodes resistance to kanamycin.

Figure 7:
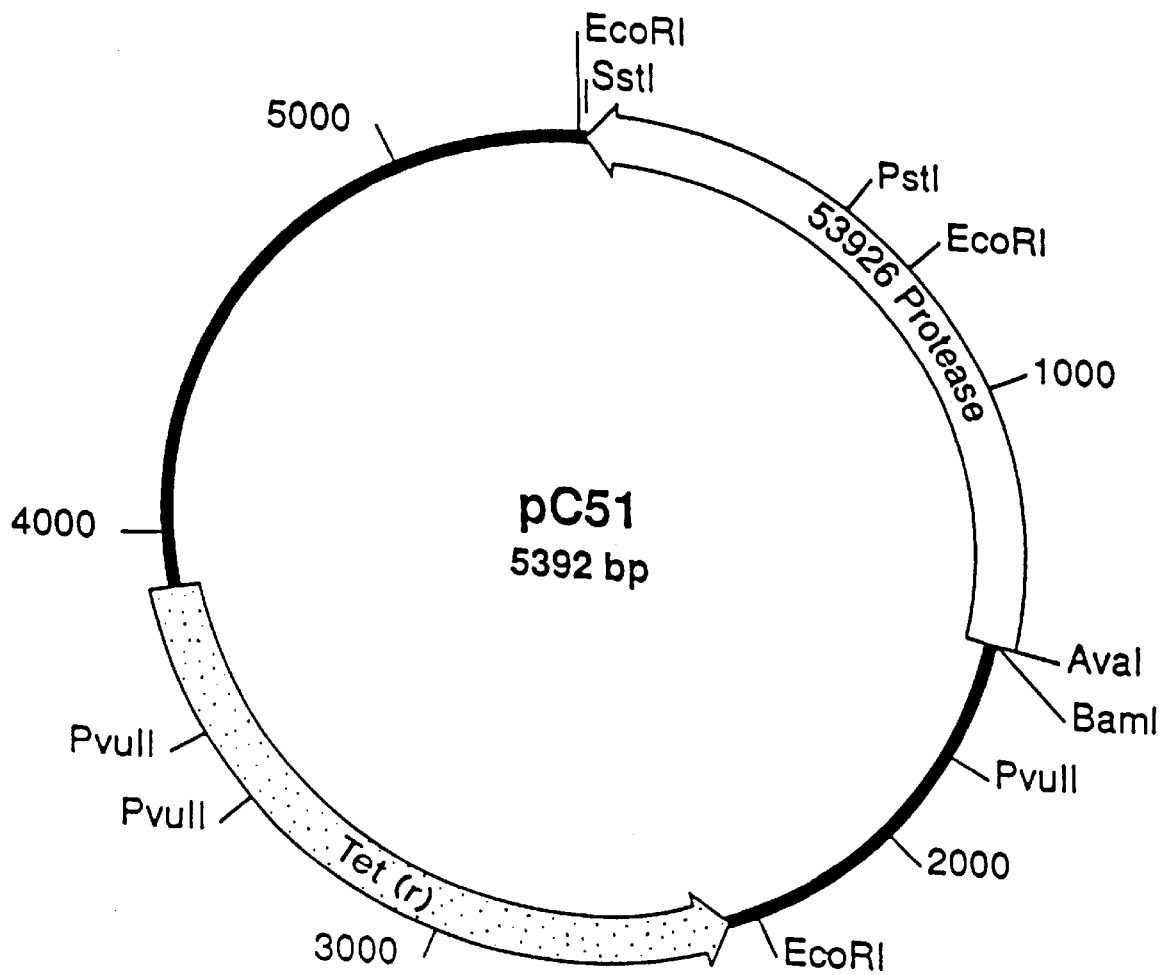

FIG. 7 shows a restriction map for Bacillus plasmid pC51 which is a derivative of plasmid pBC16 carrying the ATCC 53926 alkaline protease gene. An EcoRI/BamHI carrying the protease gene was cloned between an EcoRI site and the BamHI sites on plasmid pBC16. This plasmid is discussed in Example 3: Cloning of mutant protease genes. Plasmid pC51 encodes resistance to tetracycline.

Figure 8:
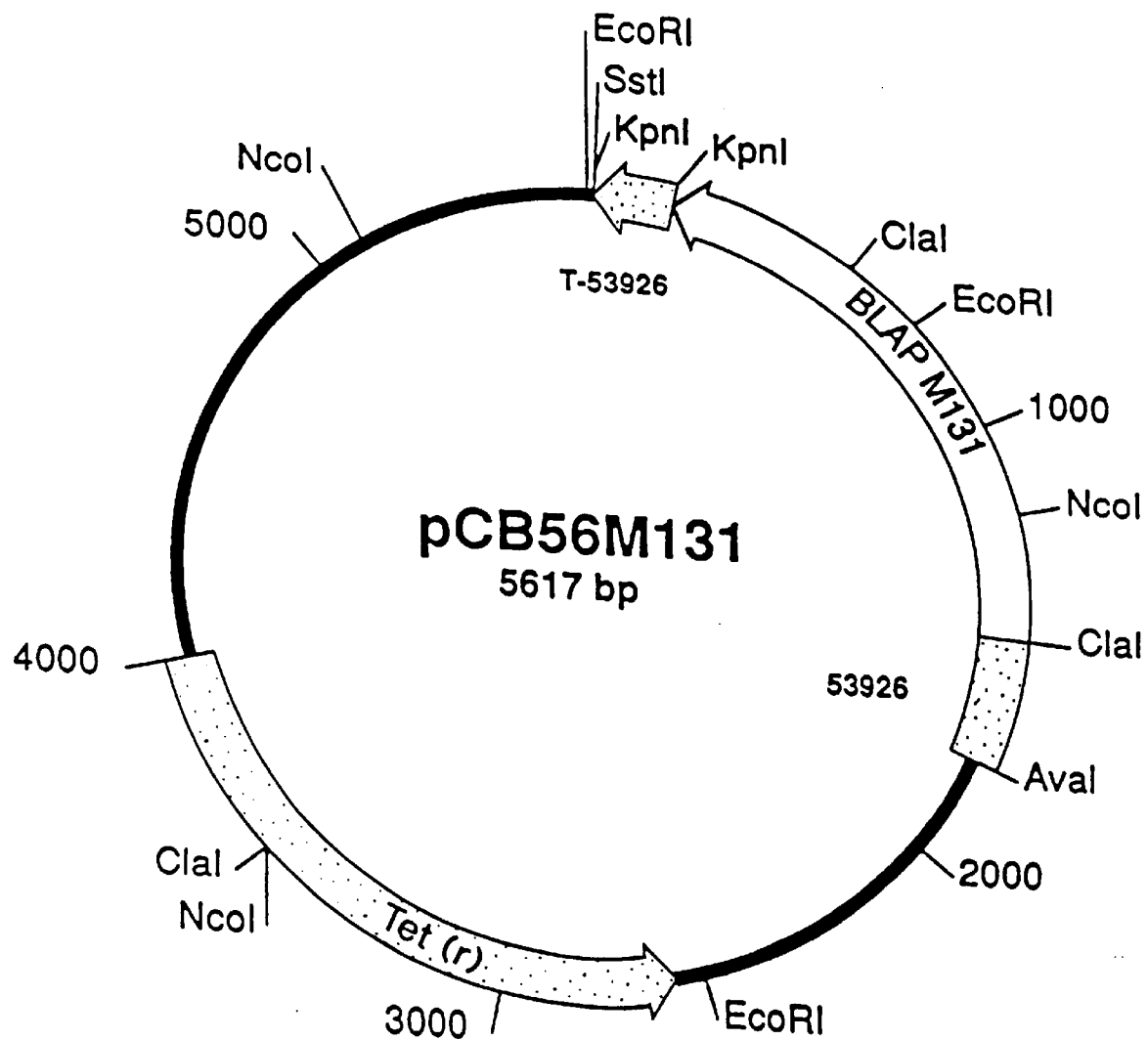

FIG. 8 shows a restriction map for Bacillus plasmid pBC56M131 which encodes the gene for BLAP variant M131. Included is the hybrid fusion between the ATCC 53926 alkaline protease gene and the BLAP gene as described in FIG. 2 for pCB13C. Also present is the transcription terminator sequence from the ATCC 53926 alkaline protease gene. This is a pBC16 based plasmid which encodes resistance to tetracycline.

Figure 9:
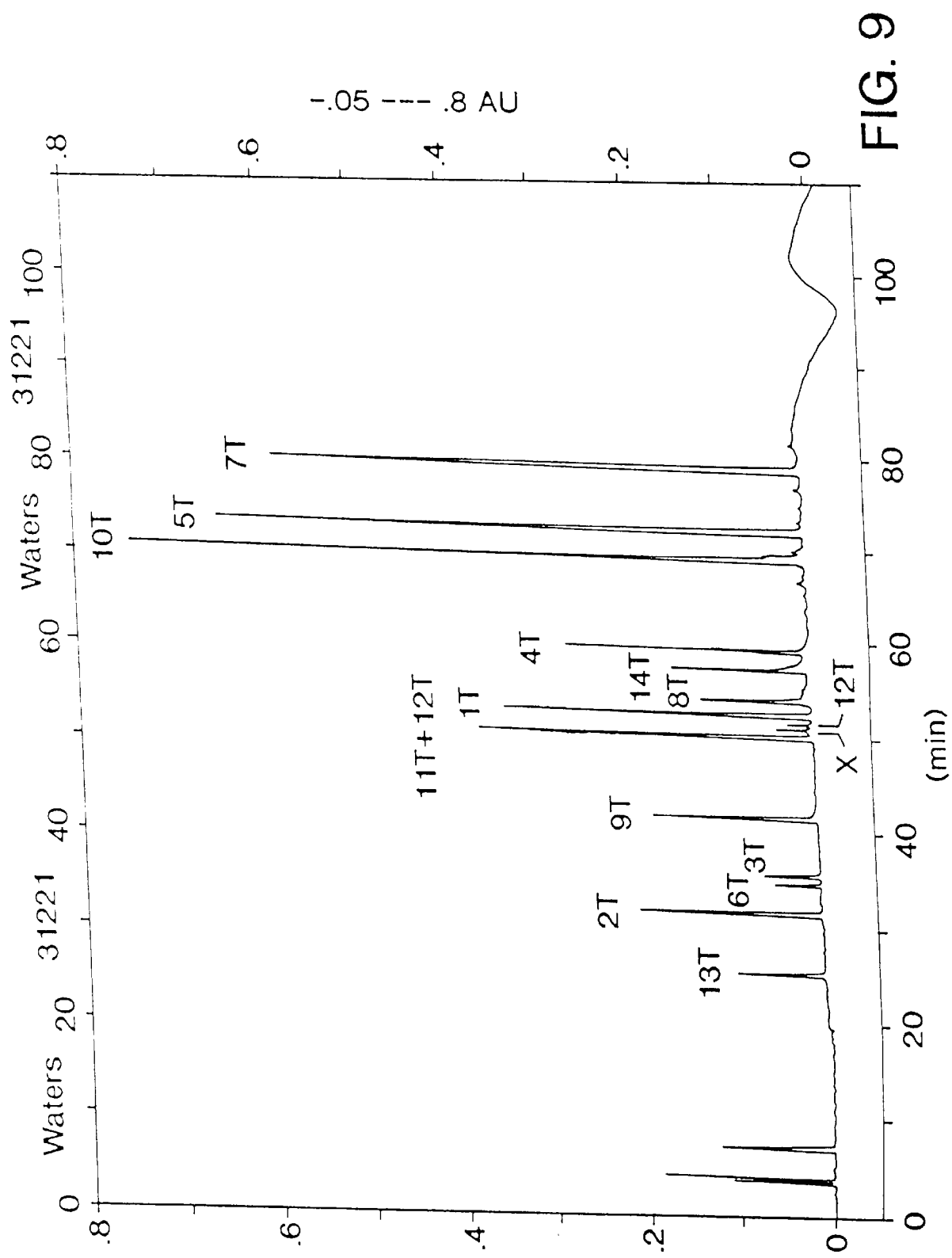

FIG. 9 shows the peptides produced by digestion of BLAP with trypsin. BLAP (11 mg/ml$^{-1}$) was digested in 1.6M urea, 0.16M NH$_4$HCO$_3$ with trypsin (1%, w/w, in 1 mM HCl) for 10 min at 37 C. The sample was then acidified with 10% (v/v) Trifluoroacetic acid (TCA) to a final concentration of 1% TCA. Peptides were separated by injecting 10 ul of sample onto an HPLC column as described in Example 8. The tryptic peptides correspond to the following BLAP sequences: Fragment #1—Ala1 to Arg10; Fragment #2—Val11 to Arg19; Fragment #3—Gly20 to Lys27; Fragment #4—Val28 to Arg44; Fragment #5—Gly45 to Lys92; Fragment #6—Val93 to Arg99; Fragment #7—Gly100 to Arg143; Fragment #8—Gly144 to Arg164; Fragment #9—Tyr165 to Arg180; Fragment #10—Ala181 to Lys229; Fragment #11—Gln230 to Lys231; Fragment #12—Asn232 to Arg241; Fragment #13—Asn242 to Lys245; and Fragment #14—Asn246 to Arg269.

BACTERIAL STRAINS

Bacillus licheniformis E312 with plasmid pBC56M131 is deposited as ATCC 68614. Escherichia coli WK6 with plasmid pMC13C is deposited as ATCC 68615. E. coli GM33 with plasmid pCB13C is deposited as ATCC 68616. E. coli WK6 with plasmid pMa5-8 is deposited as ATCC 68617. E. coli WK6 with pMc5-8 is deposited as ATCC 68618.

DESCRIPTION OF THE PREFERRED EMBODIMENTS

One aspect of the present invention relates to a method for choosing amino acid alterations which can result in a mutant protease with improved wash performance. Improved wash performance is obtained by introducing amino acid alterations within a region of the substrate binding pocket of the enzyme which results in an increased negative charge. According to the present invention, this can be achieved by increasing the number of negatively charged amino acids residues or decreasing the number of positively charged amino acid residue in the region of the substrate binding pocket of the protease within 7A of a bound substrate molecule such as AAPF. In particular, amino acid alterations at positions 99, 154 and 211 within Bacillus lentus Alkaline Protease (BLAP) variants M130 and M131 were shown to enhance the wash performance of the enzyme.

A second aspect of the present invention relates to mutant proteolytic enzymes which have an improved wash performance relative to the wild type protease as determined by laboratory tests. The mutations described in this invention are introduced into BLAP variants M130 or M131 which have been previously described in patent application Ser. No. 07/706,691 filed May 29, 1991. Both M130 and M131 have been shown to have improved stability as compared to the wild type protease. Mutant M130 contains four amino acid alterations: S3T; A188P; V193M and V199I.

Mutant M131 contains five amino acid alterations: S3T; V4I; A188P; V193M and V199I. The system used to designate preferred proteases first list the amino acid residue in the mature form of BLAP at the numbered position followed by the replacement amino acid using the accepted one letter amino acid codes. The amino acid sequences for proteases M130 and M131 are given in SEQ ID NO: 1 and SEQ ID NO: 2, respectively, contained in patent application Ser. No. 07/706,691 filed May 29, 1991. The Bacillus lentus DSM 5483 BLAP DNA and protein sequences are shown herein in SEQ ID No: 19 and SEQ ID No: 22, respectively. The M130 DNA and protein sequences are shown herein in SEQ ID No: 20 and SEQ ID No: 23, respectively. The M131 DNA and protein sequences are shown herein in SEQ ID No: 21 and SEQ ID No: 24, respectively. Both M130 and M131 served as the basis for additional amino acid alterations to achieve proteases with improved wash performance. The mutant proteases according to the invention are those derived by the replacement of at least one amino acid residue of mutant proteases M130 or M131 wherein said amino acid residue is selected from the group consisting of arginine at position 99, serine at position 154 and leucine at position 211. Table 2 provides a description of the BLAP mutant proteases claimed in the invention which include F11, F43, F44, F45, F46, F47, F49, F54 and F55. For example F11 shown in Table 2 is derived from M130 and contains an arginine at position 99 replaced by a serine (R99S) along with the other mutations present in M130 which include: a serine at position 3 replaced by a threonine (S3T); an alanine at position 188 replaced by a proline (A188P); a valine at position 193 replaced by a methionine (V193M) and a valine at position 199 replaced by a isoleucine (V199I). Of the remaining mutant proteases, F43 through F49 are derived from M131. Mutants F54 and F55 are derived from mutant F49. The amino acid sequences of the preferred proteolytic enzymes F11, F43, F44, F45, F46, F47, F49, F54 and F55 are given in SEQ ID NO: 1 to SEQ ID NO: 9, respectively, of this application.

A third aspect of this invention relates to the genes which encode the mutant proteases listed in Table 2. The genetic construction of all mutant proteases in this invention are described in detail in Example 2. In all cases the mutations introducing the amino acid alterations are constructed using known procedures. The DNA sequences encoding the mature forms of the referred proteases F11, F43, F44, F45, F46, F47, F49, F54 and F55. Each hybrid gene encoding one of the mutant proteases listed above is comprised in the direction of transcription, a promoter, a ribosomal binding site, and initiation codon and the major portion of the pre region of the B. licheniformis ATCC 53926 alkaline protease gene operably linked to a portion of the pre region and all of the pro and mature regions of a variant of the BLAP gene followed by the transcription terminator sequence for the alkaline protease gene from ATCC 53926. The hybrid gene may be integrated into the chromosome of the host or is carried on a plasmid which replicates within the Bacillus strain of choice. In particular, plasmid pUB110 or a derivative of pUB110 is the plasmid of choice for protease production in strains of Bacillus subtilis and plasmid pBC16 or a derivative of pBC16 is the choice for protease production in strains of *B. licheniformis*. The mutant proteases are produced by growing the Bacillus strains transformed by plasmids containing the hybrid genes in a suitable medium.

EXAMPLE 1

Identification of Sites in BLAP for Mutagenesis

A variety of natural subtilisins and other serine proteases were tested for their washing efficacy. The results showed that washability relates to the number and distribution of charged amino acid residues in the substrate binding region. An improvement in the wash performance was seen with an increased number of negatively charged amino acid residues or with a decrease of the number of positively charged amino acid residues in the substrate binding region. Accordingly, the BLAP mutants claimed herein have a reduced positive net charge in the substrate binding region and they show improved washability.

Improved wash performance was obtained by introducing amino acid alterations within the substrate binding pocket which resulted in a variation in charge. Alterations were made for amino acids residing within the substrate binding pocket of either BLAP variant M130 or BLAP variant M131.

Figure 1:
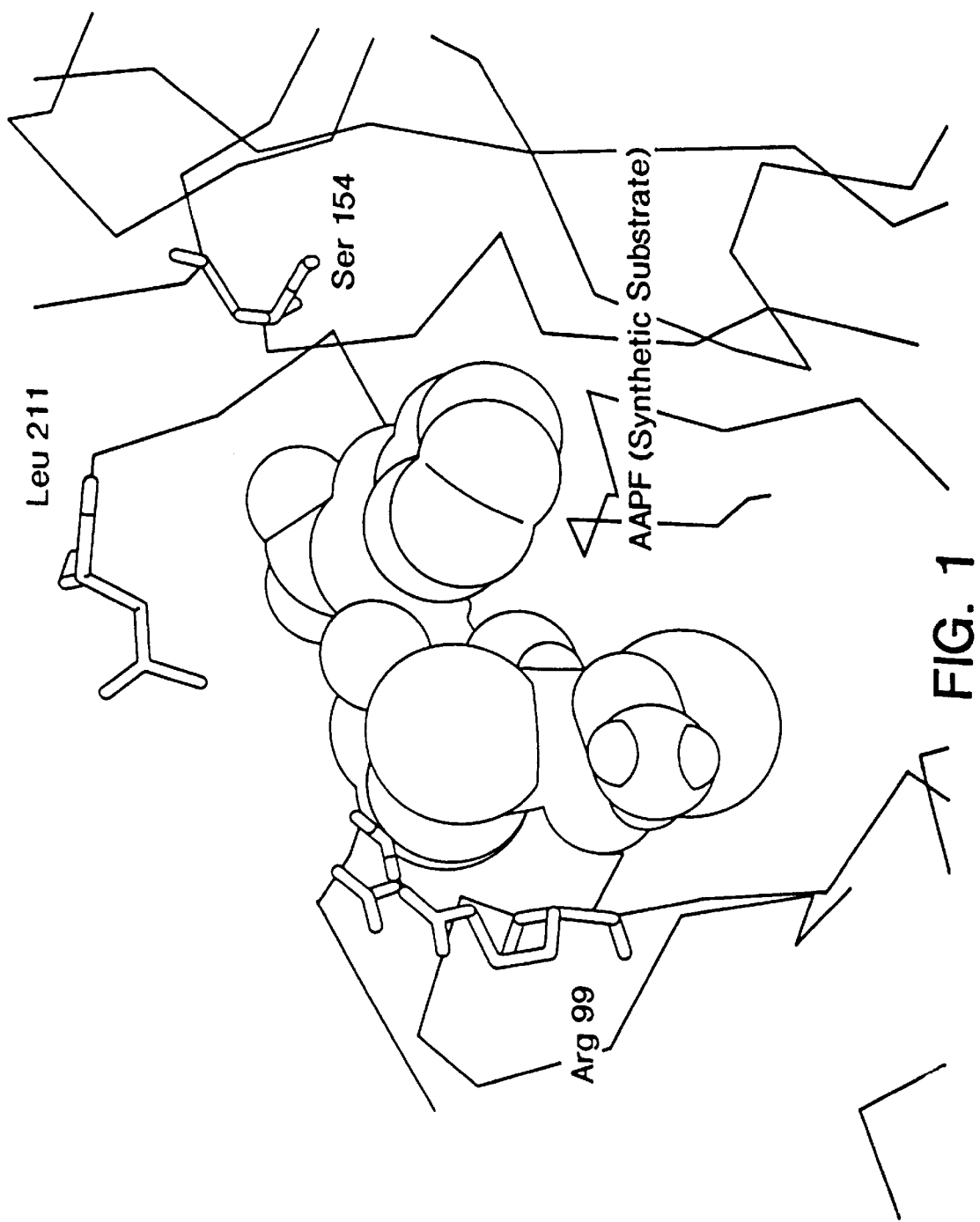
FIG. 1 is a model of the substrate binding region of wild type BLAP with the synthetic substrate AAPF bound to the enzyme. The positions of arginine 99, serine 154 and leucine 211 in relation to the bound substrate are shown.

The substrate binding pocket of these enzymes is defined as the region within 7 Å of a bound substrate molecule, AAPF. FIG. 1 shows the characteristic structure of the substrate binding pocket of wild type BLAP with the synthetic substrate AAPF. AAPF bound to the enzyme was modeled on crystallographic data of subtilisin-inhibitor complexes found in the literature and available from the Brookhaven Protein Data Bank. The structure of BLAP variants M130 and M131 within the substrate binding pocket is essentially identical to wild type BLAP based upon Xray crystallography. The structure of wild type BLAP to a 1.4 Å resolution has been published in patent application Ser. No. 07/706,691 filed May 29, 1991 and the corresponding atomic coordinates deposited with the Brookhaven Protein Data Bank. In particular, amino acid alterations at positions 99, 154 and 211 within BLAP variants M130 and M131 were shown to enhance the wash performance of the enzyme. The parental amino acids occupying these sites, Arginine 99, Serine 154, and Leucine 211 are depicted in FIG. 1. All three amino acids are located within the specified 7 Å radius of AAPF.

EXAMPLE 2

Construction of Mutant Genes of the BLAP Gene

A. Construction of Mutants M130 and M131

Genes which express the mutant *B. lentus* DSM 5483 proteases according to the invention are made by altering one or more codons of the wild-type *B. lentus* DSM 5483 alkaline protease gene. Protease M130 was derived from BLAP by introducing mutations S3T, A188P, V193M and V199I.

Protease M131 was derived from BLAP by introducing the mutations S3T, V4I, A188P, V193M, and V199I. Genes encoding proteases M130 and M131 were constructed using the pMac procedure (Stanssens, P., Opsomer, C., McKeown, Y. M., Kramer, W., Zabeau, M., and Fritz, H.-J. (1989) Nucleic Acids Res. 17, 4441–4445). Proteases M130 and M131 have been previously described in patent application Ser. No. 07/706,691 filed May 29, 1991. Proteases M130 and M131 exhibit improved thermal and surfactant stability over the wild type BLAP and served as the basis for developing proteases with improved wash performance. The genetic techniques used to modify the BLAP gene to produce the M130 and M131 proteases have also been described in patent application WO 91/02792. The description in WO 91/02792 incorporated herein by reference for purposes of indicating the state of the art.

Figure 2:
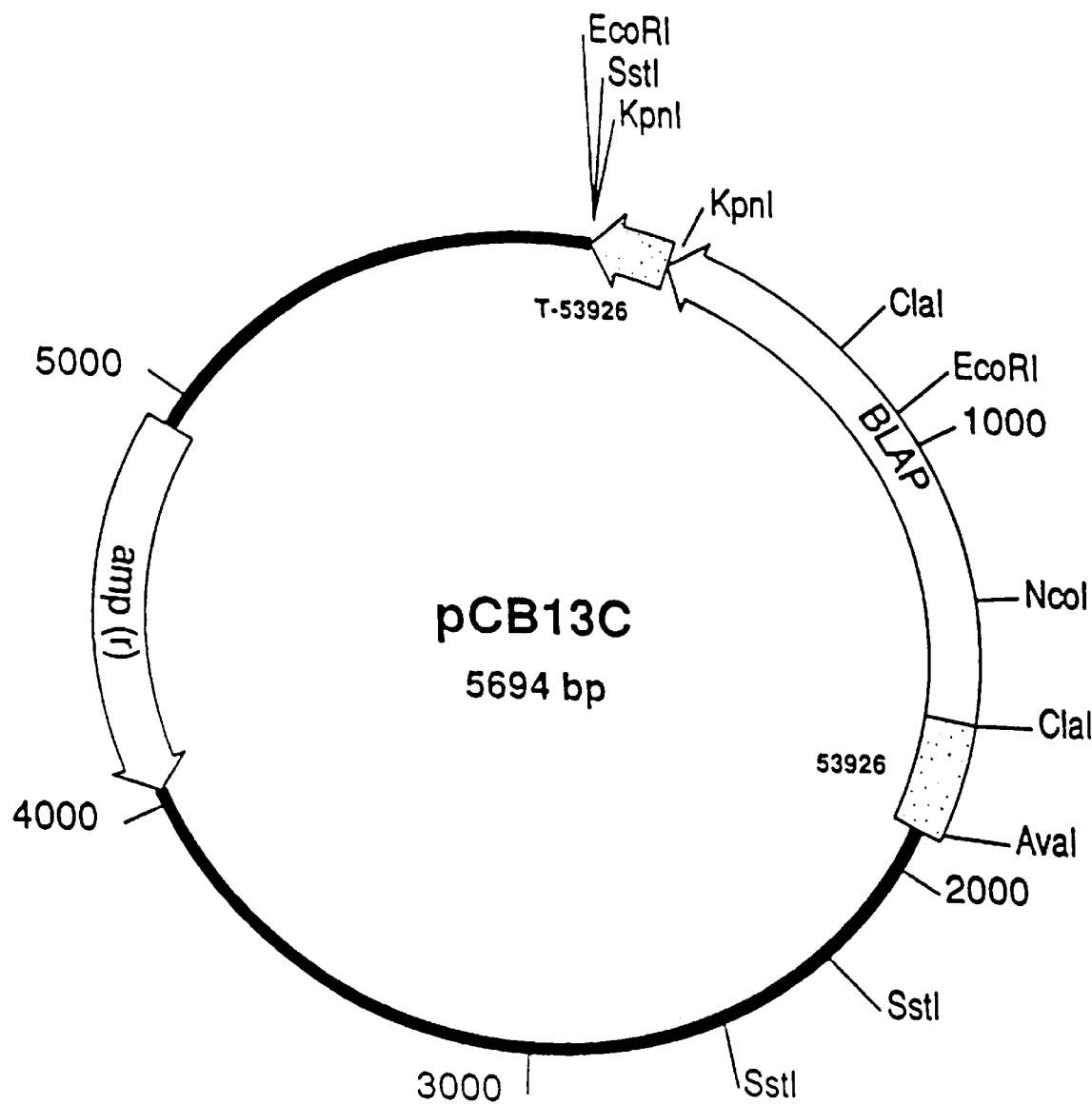
FIG. 2 shows the restriction map for *Escherichia coli* plasmid PCB13C which contains a hybrid gene fusion between the *Bacillus licheniformis* ATCC 53926 protease gene and the *Bacillus lentus* DSM 5483 BLAP gene. The promoter, ribosomal binding site and presequence (53926) from ATCC 53926 were fused to the pro and mature sequence of the BLAP gene. The transcription terminator of ATCC 53926 (T-53926) was appended to the BLAP coding sequence.

Proteases M130 and M131 were derived from the *B. lentus* DSM 5483 alkaline protease (BLAP) by site-specific mutagenesis of DNA encoding the mature form of wild type BLAP. The DNA fragment encoding the mature form of wild type BLAP was prepared using plasmid pCB13C (FIG. 2). Plasmid pCB13C contains a hybrid fusion between the *B. licheniformis* ATCC 53926 protease gene and the *B. lentus* DSM 5483 BLAP genes. Specifically, this hybrid fusion contains DNA encoding the promoter, ribosomal binding site, and 21 residues of the pre sequence from the ATCC 53926 protease gene fused to a DNA sequence encoding the last five residues of the BLAP pre sequence and all of the pro and mature residues of BLAP. This fusion is referred to as the ClaI fusion because this restriction site is located at the juncture between the ATCC 53926 and DSM 5483 DNA's. A new ClaI restriction site had to be introduced into the ATCC 53926 alkaline protease gene near to the junction of the pre and pro sequences. The ClaI site was introduced into the ATCC 53926 alkaline protease gene by using the polymerase chain reaction (PCR) to amplify a DNA fragment containing sequence information from the N-terminal part of the ATCC 53926 alkaline protease gene. The amplified fragment included the ATCC 53926 alkaline protease promoter, ribosomal binding site, initiation codon, and most of the pre sequence. The DNA sequence of this fragment is shown in FIG. 3. This 292 bp DNA fragment was flanked by AvaI and ClaI restriction sites at its 5' and 3' ends, respectively. The BLAP gene already contained a naturally occurring ClaI site at the corresponding position. Analysis of the DNA sequence across the fusion of the ATCC 53926 and BLAP genes confirmed the expected DNA and amino acid sequences.

Figure 4:
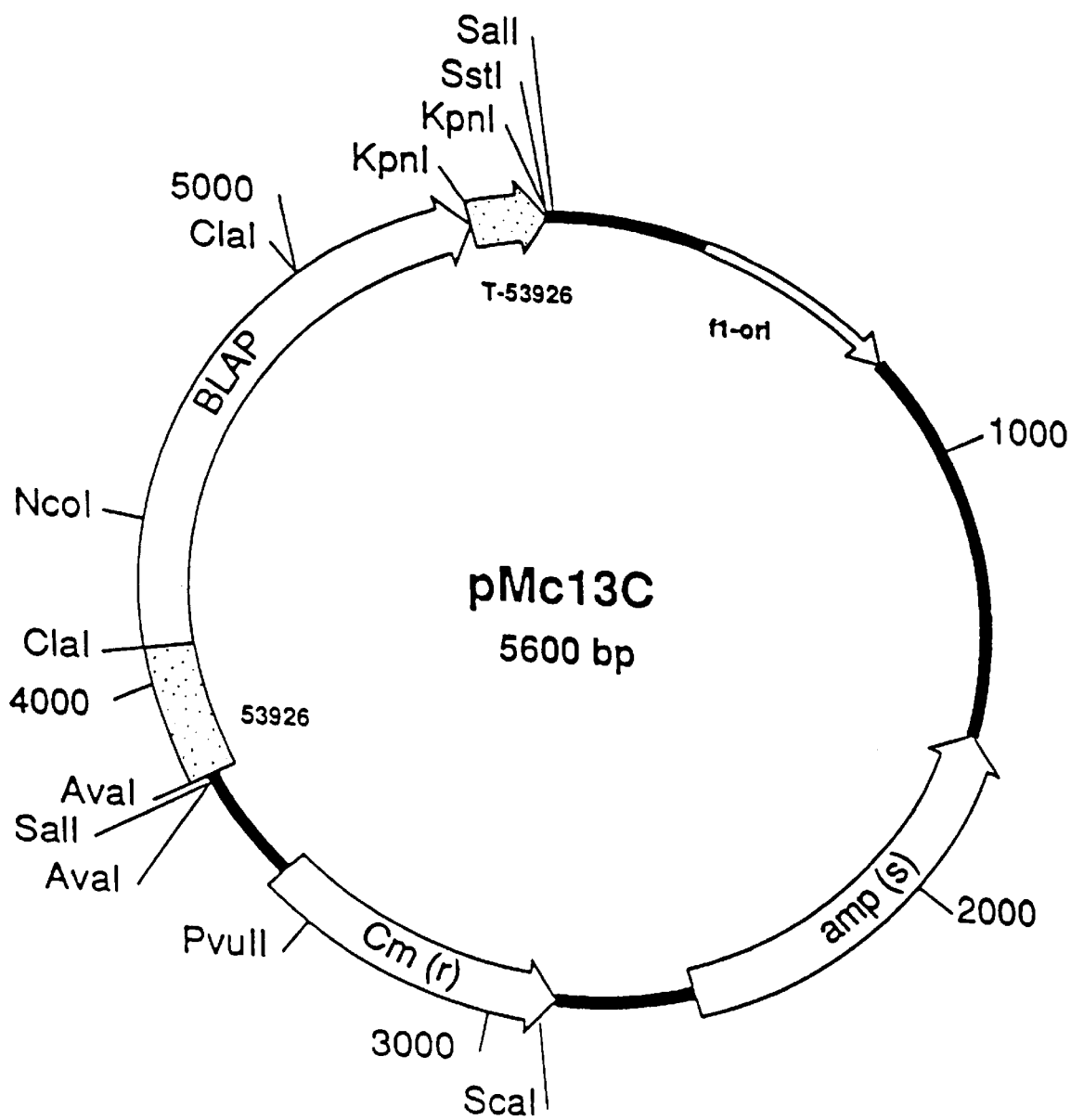
FIG. 4 shows the restriction map for *E. coli* plasmid pMc13C which is derived from pMac5-8 and contains the BLAP gene. The ampicillin resistance ($Ap^R$) gene present in pMc13C carries an amber mutation which renders it inactive.

To perform mutagenesis the BLAP gene is subcloned into the mutagenesis vector pMa5-8. This is accomplished by synthesizing a DNA fragment containing the ClaI fusion gene and the ATCC 53926 transcription terminator as a SalI cassette using the PCR. The PCR was carried out using conditions as described by the manufacturer (Perkin Elmer Cetus, Norwalk, Conn.). In the PCR, two synthetic oligonucleotides bearing SalI sites are used as primers and *Escherichia coil* vector pCB13C DNA as a template. After cutting the PCR product with SalI, this fragment is cloned into the mutagenic plasmid pMc5-8 which has previously been cut with SalI and dephosphorylated with bacterial alkaline phosphatase. Plasmids pMc5-8, and pMa5-8 were obtained from H.-J. Fritz and are described by Stanssens, P., et al. (1989) Nucleic Acids Res. 17, 4441–4454. SalI sites are chosen to allow the PCR fragment to be cloned into pMc5-8 in both orientations. The ligation mix is transformed into *E. coli* WK6. Chloramphenicol resistant ($Cm^R$) transformants are screened for the presence of an insert and a correct plasmid construct pMc13C is identified as shown in FIG. 4. Once the gene is cloned into the pMc5-8 vector and desirable sites for mutation are identified, the mutation(s) is introduced using synthetic DNA oligonucleotides according to a modification of a published protocol (Stanssens, P., et. al. (1989) Nucleic Acids Res. 17, 4441–4454). The oligonucleotide containing the mutation(s) to be introduced is annealed to a gapped duplex (gd) structure which carries the BLAP gene on a segment of single stranded (ss) DNA. The gapped duplex can be formed by annealing linear ss DNA from pMc13C with denatured and restricted pMa5-8 DNA.

Plasmid pMa5-8 contains an active ampicillin resistance gene but has an inactivating point mutation in the chloramphenicol resistance gene, whereas plasmid pMc13C contains, in addition to an intact BLAP gene, an active chloramphenicol resistance gene, but has an inactivating point mutation in the ampicillin resistance gene. The annealed product is the gd DNA which is a double stranded heteroduplex with a ss DNA gap spanning the entire cloned BLAP gene. The mutant oligonucleotide is able to anneal to homologous ss BLAP DNA within the gap and the remaining gap is filled in by DNA polymerase I (Klenow fragment) and ligated using T4 DNA ligase (New England Biolabs Inc., Beverly, Mass. [NEB]). The mutagenic efficiency of such a system can be improved by the use of Exonuclease III (Exo III, NEB). Exo III is an exodeoxyribonuclease that digests double stranded DNA from the 3' end. As a free 3' end is required, closed circular ss DNA or ds DNA is unaffected by this enzyme. A subsequent treatment of the product of the fill-in reaction with Exo III removes any species with only partially filled gaps. This significantly improves the mutagenic efficiency and is the preferred mutagenesis method. The product of the fill-in reaction is then transformed into a repair deficient E. coli strain (WK6mutS) and ampicillin resistant transformants ($Ap^R$) are selected. Replication of the transformed heteroduplex plasmid results in two different progenies. One progeny contains the wild type BLAP gene and the intact chloramphenicol resistance gene, but an inactive ampicillin resistance gene. The other progeny contains a BLAP gene carrying the mutation of interest and is resistant to ampicillin but not to chloramphenicol.

Selection of $Ap^R$, $Cm^S$ mutant transformants with ampicillin is not sufficient to stop some background growth of the $Ap^S$, $Cm^R$ progeny carrying the wild type BLAP gene.

Therefore, it is necessary to perform a second transformation into E. coli using plasmid DNA prepared from the $Ap^R$ transformants of the WK6mutS strain. This second transformation uses a low plasmid concentration with a large number of recipient cells of a suppressor deficient strain of E. coli such as WK6. This approach decreases the likelihood of a recipient cell receiving plasmid DNA from both progeny. $Ap^R$ transformants are selected and plasmid DNA from several transformants is isolated and screened for the presence of the mutation. The pMa mutant derivative of the first mutagenesis round can be used for a second round of mutagenesis by preparing ss DNA of that species and annealing it to XbaI/HindIII restricted and denatured DNA of pMc5-8. Plasmid pMc5-8 is identical to pMa5-8 except that it contains an active chloramphenicol resistance gene and an inactive ampicillin resistance gene. The general procedure is the same as that described above. The construction of the genes encoding proteases M130 and M131 required two rounds of mutagenesis. In the first round of mutagenesis an oligonucleotide was designed to introduce mutations A188P, V193M, and V199I. In a second round of mutagenesis an oligonucleotide was designed to introduce mutation S3T in the case of M130 and mutations S3T and V4I in the case of M131. The presence of all of these mutations was verified by DNA sequencing.

B. Construction of Genes Encoding New Proteases with Improved Wash Performance.

Mutations R99G, R99A, R99S, S154D, S154E and L211D were introduced into the gene encoding M131 protease using PCR mutagenesis by overlap extension. Mutation R99S was introduced into the gene encoding protease M130 using PCR mutagenesis by overlap extension. Construct pCB76M131 (FIG. 5) was used to construct mutants F43, F44, F45, F46, F47, and F49 (Table 2). Construct pCB76M130 was used to construct mutant F11 and construct pCB76F49 (a newly constructed mutant) was used to construct mutants F54 and F55.

TABLE 2

Description of BLAP Mutants

| | |
|---|---|
| BLAP | wild type enzyme |
| M130 | S3T + A188P + V193M + V199I |
| M131 | S3T + V4I + A188P + V193M + V199I |
| F11 | S3T + R99S + A188P + V193M + V199I |
| F43 | S3T + V4I + R99G + A188P + V193M + V199I |
| F44 | S3T + V4I + R99A + A188P + V193M + V199I |
| F45 | S3T + V4I + R99S + A188P + V193M + V199I |
| F46 | S3T + V4I + S154E + A188P + V193M + V199I |
| F47 | S3T + V4I + S154D + A188P + V193M + V199I |
| F49 | S3T + V4I + A188P + V193M + V199I + L211D |
| F54 | S3T + V4I + R99G + A188P + V193M + V199I + L211D |
| F55 | S3T + V4I + S154E + A188P + V193M + V199I + L211D |

Materials required to perform this procedure include: A DNA Thermal Cycler (Perkin Elmer Cetus); GeneAmp kit (Perkin Elmer Cetus); AmpliWax (Perkin Elmer Cetus); and 0.5 ml sterile polypropylene tubes (Perkin Elmer Cetus); Microcon-100 concentrators (Amicon, Beverly, Mass.); TE buffer (10 mM tris-(hydroxymethyl)aminomethane [Tris], 1 mM disodium ethylenediamine tetraacetic acid (EDTA), adjusted to pH 8 with 2 N HCl); Minigel electrophoresis apparatus (Hoefer Scientific, San Francisco, Calif.); 1% (w/v) SeaKem agarose gel (FMC, Rockland, Me.) in TBE buffer (0.089 M Tris, 0.089 M boric acid, 2 mM EDTA); 0.5 $\mu g \cdot ml^{-1}$ ethidium bromide in water; restriction enzymes NheI (NEB), XbaI (NEB); and SstI (BRL, Gaithersburg, Md.).

PCR's were carried out using the GeneAmp kit and AmpliWax as specified by the manufacturer. They were subjected to 1 cycle of denaturation (3 minutes, 95° C.), annealing (2 minutes, 50° C.) and extension (2 minutes, 72° C.) and 30 cycles of denaturation (1 minute, 94° C.), annealing (1 minutes, 50° C.) and extension (1 minute, 72° C.) using a DNA Thermal Cycler. Each cycle was extended for 10 sec at 72° C.

Site-directed mutagenesis by overlap extension is described by (Ho, S. N., Hunt, H. D., Horton, R. M., Pullen, J. K., and Pease, L. R. (1989) Gene 77, 51–59). For BLAP mutants F43, F44, F45, F46, F47 and F49 10 ng of pCB76M131 plasmid DNA was used as template for the initial round of mutagenesis. For BLAP mutant F11 10 ng of pCB76M130 plasmid DNA was used as template, and for BLAP mutants F54 and F55 10 ng of pCB76F49 DNA was used as template. The pUB110 forms of these plasmids were chosen because they provide higher yields of protease in the B. subtilis DB104 host than the pBC16 forms of the plasmids. PCR fragments were checked by agarose gel electrophoresis and cleaned using a Microcon-100 concentrator (Amicon) after each round of PCR. After the second round of PCR, the fragments were digested with either NheI/XbaI or NheI/SstI (depending on the location of the intended mutation) and cloned back into pCB76M131 DNA in the case of mutants F43, F44, F45, F46, F47 and F49, pCB76M130 DNA in the case of mutant F11 and pCB76F49 in the case of mutants F54 and F55 using B. subtilis DB104 competent cells as previously described. Plasmid DNA isolation was accomplished using ion exchange minicolumns (QIAGEN, Inc., Chatsworth, Calif.) and mutations were checked by Sanger ds DNA sequencing as previously described.

EXAMPLE 3

Cloning of Mutant Protease Genes

A. Cloning of Mutant Proteases Produced via the pMac System.

Proteases M130 and M131 can be produced by transferring the respective gene encoding either M130 or M131 from the particular *E. coli* pMc13C derivative vector into a plasmid vector which can replicate in Bacillus. To accomplish this, the desired mutant gene is separated from the appropriate pMc13C plasmid by digestion with the restriction endonucleases AvaI and SstI, followed by ligation to the larger AvaI/SstI fragment from either plasmid pH70 (FIG. 6) or pC51 (FIG. 7). These AvaI/SstI fragments from pH70 and pC51 include the DNA sequences necessary for replication in Bacillus and encode either kanamycin resistance ($Km^R$) or tetracycline resistance ($Tc^R$), respectively. Plasmid pH70 is constructed by cloning the ATCC 53926 alkaline protease gene carried on a EcoRI/BamHI DNA fragment into the $Km^R$ plasmid pUB110 between the EcoRI and BamHI sites. Plasmid pC51 is constructed by cloning the ATCC 53926 protease gene carried on a EcoRI/BamHI fragment into the $Tc^R$ plasmid pBC16 between the EcoRI and BamHI sites. The larger AvaI/SstI fragment from either pH70 or pC51 used for cloning the DNA fragment encoding either M130 or M131 is first purified from other plasmid DNA fragments by high pressure liquid chromatography (HPLC) on an anion exchange column (Gen-Pak FAX, 4.6 mm diameter, 100 mm long; Waters, Milford, Mass.).

Conditions for elution of the DNA are a flow rate of 0.75 ml·min$^{-1}$ with a gradient from 50% of Buffer A (25 mM Tris, containing 1 mM EDTA and adjusted to pH 8.0 with 2 N HCl) and Buffer B (25 mM Tris, containing 1 mM EDTA, 1 M NaCl, and adjusted to pH 8.0 with 2 N HCl) to 30% of Buffer A and 70% of Buffer B in 30 min.

The two ligated DNA's are transformed into *B. subtilis* DB104. The genes encoding the major alkaline and neutral proteases present in this strain have been inactivated (Kawamura, F. and Doi, R. A. (1984) J. Bacteriol. 160, 442–444). Cells of *B. subtilis* DB104 transformed by these plasmids grow on a nutrient-skim milk agar in the presence of either kanamycin or tetracycline.

Transformants of DB104 that manufacture mutant protease are identified by the formation of clear zones of hydrolysis in the skim milk. Confirmation that the protease-producing transformants carry a plasmid-borne M130 or M131 gene with the desired mutation(s) is accomplished by purifying plasmid DNA from a culture of each transformant. The plasmid DNA is purified away from cell protein and chromosomal DNA by SDS-salt precipitation followed by chromatography over a QIAGEN ion-exchange column (QIAGEN,Inc., Chatsworth, Calif.). AvaI/SstI digested plasmid DNAs from different transformants are compared with AvaI/SstI-digested derivatives of plasmid pH70 or pC51 known to carry an intact BLAP gene. Restriction digests of these plasmids are compared by agarose gel electrophoresis to identify plasmids that have the proper-sized AvaI/SstI DNA fragments. Selected plasmid DNAs are then sequenced across the region of the expected M130 or M131 mutations to confirm that the desired mutation(s) are present. Genes M130 and M131 cloned into the derivative of plasmid pC51 (TcR) are designated plasmids pCB56M130 and pCB56M131 respectively (FIG. 8), while the same genes cloned into a derivative of plasmid pH70 are designated plasmids pCB76M130 and pCB76M131 respectively (FIG. 5). One or more clones of each BLAP mutation are stored frozen in 15% glycerol at −70° C. and also cultivated in shake flasks to produce mutant protease for characterization.

B. Cloning of Mutant Proteases Produced via PCR Overlap Procedure.

As described above, the amplified PCR fragments are cloned back into plasmids pCB76M130, pCB76M131 or pCB76F49.

For expression in the *B. licheniformis* production strain the AvaI/SstI fragment carrying the modified M130, M131 or F49 genes is cloned back into the pC51 type vector as described previously.

EXAMPLE 4

Production of Mutant Proteases

Wild type BLAP protein and mutant proteins were produced by transformed *Bacillus subtilis* DB 104 in shake flasks. A hot loop was used to streak each mutant strain from a frozen cryovial culture onto an LB-skim milk agar containing either 20 µg·ml$^{-1}$ of kanamycin or 15 µg·ml$^{-1}$ of tetracycline. The plates were incubated at 37° C. for 20 to 24 hours. A single, isolated colony producing a good zone of hydrolysis of the skim milk was picked into a 250 ml Erlenmeyer flask containing about 50 ml Luria Broth (LB) which contained either 20 µg·ml$^{-1}$ kanamycin or 15 µg·ml$^{-1}$ of tetracycline. The broth was incubated in a New Brunswick Series 25 Incubator Shaker at 37° C. with shaking at 280 rpm for 7 to 8 hours. Either 2.5 ml of the turbid preculture was transferred into 50 ml of MLBSP containing either 20 µg·ml$^{-1}$ kanamycin or 15 µg·ml$^{-1}$ of tetracycline in each of four baffled 500 ml flasks, or 5 ml of preculture was used as an inoculum for 100 ml of MLBSP broth with antibiotic contained in each of two 500 ml baffled flasks (a 5%, v/v, transfer). All flasks were incubated at 240 rpm and 37° C. for 64 hours. After 64 hours of incubation the content of a set of flasks for each culture was consolidated, transferred to 50 ml centrifuge tubes, and centrifuged at 20,000× $g_{av.}$ for 15 minutes at 4° C. The broth was filtered through Miracloth (Calbiochem Corp., #475855) into 400 ml beakers placed on ice. The pH of the solution was adjusted to 5.8 by the addition of glacial acetic acid. After 30 minutes of stirring fine debris were removed by centrifugation at 20,000×$g_{av.}$ for 15 minutes. The volume of the supernatant was recorded. Aliquots of 1 ml were set aside for analysis by native and denaturing polyacrylamide gel electrophoresis (PhastSystem, Pharmacia), for determination of total proteolytic activity by the HPE method, and for active site titration. The broth was stored on ice until the protease could be purified. For long-term storage or for shipment the broth was mixed with an equal volume of propane-1,2-diol. The composition of the MLBSP media used for the production of BLAP in shake flask cultures is described in Table 3.

TABLE 3

| Composition of MLBSP Media[1] | |
|---|---|
| Component | Quantity (for 1 liter of media) |
| deionized water | 750 ml |
| Difco Casitone | 10 g |
| Difco Tryptone | 20 g |
| Difco Yeast Extract | 10 g |

TABLE 3-continued

Composition of MLBSP Media[1]

| Component | Quantity (for 1 liter of media) |
| --- | --- |
| NaCl | 5 g |
| Sodium Succinate | 27 g |

[1]The pH of the media was adjusted to 7.2 with 2 N NaOH, the volume was brought to 815 ml with water, and the solution was autoclaved for 15 minutes at 121° C. at a pressure of 15 pounds per square inch. After cooling the sterile stock solutions described in Appendix 1 were added with stirring. Either a kanamycin or tetracycline stock solutions was added to the media just before use to a final concentration of 20 $\mu$g · ml$^{-1}$ and 15 $\mu$g · ml$^{-1}$, respectively.

APPENDIX 1

(Additions to MLBSP Broth)

| Component | Quantity (for 1 liter of media) | |
| --- | --- | --- |
| MgSO$_4$ · 7H$_2$O | (100 mg · ml$^{-1}$ stock) | 1.0 ml |
| CaCl$_2$ · 2H$_2$O | (30 mg · ml$^{-1}$ stock) | 2.5 ml |
| FeSO$_4$ · 7H$_2$O | (1 mM stock) | 0.5 ml |
| MnCl$_2$ · 4H$_2$O | (1 mM stock) | 0.5 ml |
| Glucose | (25% (w/v) stock) | 80.0 ml |
| PIPES Buffer[1] | (pH 7.2, 1 M stock) | 50.0 ml |
| Phosphate Buffer[2] | (pH 7.0, 1.5 M stock) | 50.0 ml |

[1]Piperazine-N,N'-bis(2-ethane sulfonic acid).
[2]A sufficient amount of 1.5 M dibasic phosphate (K$_2$HPO$_4$) was added to 200 ml of 1.5 M monobasic phosphate (KH$_2$PO$_4$) to adjust the pH to 6.0 using a pH meter (Beckman, model pHI44) equipped with a combination electrode (Beckman, model #3952C). The final pH was adjusted to 7.0 with 4 M KOH. All stock solutions were autoclaved at 121° C., 15 psi for 15 min except for the FeSO$_4$ · 7H$_2$O which was filter sterilized using a 0.22 $\mu$m filter system (Costar 8301).

EXAMPLE 5

Purification of BLAP and its Mutant Proteins

If not mentioned otherwise, all subsequent steps were performed on ice or at 4° C. Broth samples as obtained in Example 3 were filtered through a 0.2 $\mu$m filter, and the filtrate was concentrated by ultrafiltration. The retaining membrane had a nominal molecular-weight-cut-off of 10,000 mounted in a Minitan cassette (Millipore) or in a ultrafiltration cell (Amicon). For subsequent shipment or extended storage broth solutions were mixed with an equal volume of propane-1,2-diol to stabilize the protease.

Otherwise, the concentrate was dialyzed for 16 hours against 20 mM sodium phosphate, pH 7.0 ('phosphate buffer'), or against 20 mM N-(2-hydroxyethyl)piperazine-N'-(2-ethanesulfonic acid) (HEPES), containing 1 mM CaCl$_2$ and adjusted to pH 7.8 with NaOH ('HEPES buffer'). The dialysate was clarified by centrifugation (20,000×g$_{av.}$ for 10 minutes) and the pH of the solution, if necessary, was re-adjusted. The samples dialyzed against phosphate buffer were equilibrated for 15 minutes with 5% (w/v) DEAE-cellulose previously equilibrated in the same buffer to trap negatively charged proteins. After removal of the DEAE-cellulose by centrifugation or filtration the supernatant was loaded onto a cation exchange column (S-Sepharose Fast Flow, Pharmacia; 16 mm diameter, 90 mm long, 18 ml bed volume, 50 ml·h$^{-1}$ flow rate) previously equilibrated with phosphate buffer. The samples dialyzed against HEPES buffer were applied directly to a cation exchange column (S-Sepharose Fast Flow, Pharmacia; 15 mm diameter, 75 mm long, 13 ml bed volume, 50 ml·h$^{-1}$ flow rate) previously equilibrated with HEPES buffer. When all colored by-products were eluted the column was washed with 3 to 5 column volumes of application buffer. Protease was eluted from the cation exchanger by including 1.0 M NaCl into phosphate buffer or 0.25 M NaCl into HEPES buffer. Fractions containing the active enzyme were pooled.

The enzyme purified in phosphate buffer was concentrated and desalted by ultrafiltration using Centricon tubes (molecular-weight-cut-off 10,000; Amicon).

The protein concentration was determined by the bicinchoninic acid method (BCA method, Pierce Chemical Co., Rockford, Ill.). For stabilization of the protease 50% (v/v) propane-1,2-diol was added to the stock solution.

The pooled fractions with enzyme purified in HEPES buffer were mixed with a 5 to 8-fold volume excess of acetone at −20° C. The protein was allowed to precipitate for 4 minutes, and the mixture was centrifuged for 4 minutes at 6,600×g$_{av.}$ The supernatant was discarded, the pellet was briefly exposed to vacuum (water aspirator) to remove most of the acetone, and the pellet was dissolved in 20 mM 2-(N-morpholino)ethanesulfonic acid (MES), containing 1 mM CaCl$_2$ and adjusted to pH 5.8 with 2 N NaOH, to give an approximate protein concentration of 30 mg·ml$^{-1}$.

The solution was clarified by centrifugation in an Eppendorf centrifuge for 3 minutes at full speed (13,000×g$_{max}$) and stored frozen until used. The protein concentration was determined by the biuret method (Gornall, A. G., Bardawill, C. S., and David, M. M. (1948) J. Biol. Chem. 177, 751–766).

EXAMPLE 6

Determination of Active Protease

The active enzyme concentration was determined by active site titration with the inhibitor phenylmethyl sulfonylfluoride. A protease solution was prepared in 10 mM sodium phosphate, pH 6.5, at an approximate concentration of 100 $\mu$M based on protein determination. Inhibitor concentrations were equivalent to an estimated molar ratio of 0.25, 0.5, 0.75, 1.0 and 1.25. The mixtures were allowed to react for one hour at room temperature. Residual enzyme activity was measured spectrophotometrically by the AAPF-pNA method (see below).

EXAMPLE 7

Determination of Proteolytic Activity

Two different protease assays were used. With the HPE method protease activity was established at a single concentration of casein as substrate. In the AAPF-pNA assay initial rates of succinyl-L-alanyl-L-alanyl-L-prolyl-L-phenylalanyl-p-nitroanilide (AAPF-pNA; Bachem Bioscience, Philadelphia, Pa.) supported catalysis were used to determine the kinetic parameters $K_m$, $k_{cat}$, and $k_{cat}/K_m$.

A. Protease Assay by the HPE Method

Proteolytic activity was determined by a discontinuous assay using casein as a substrate. The final concentrations of the substrate solution were 12 mg·ml$^{-1}$ of casein (prepared according to Hammarsten; Merck, Darmstadt, #2242) and 30 mM Tris in synthetic tap water. Synthetic tap water is a solution of 0.029% (w/v) CaCl$_2$.2H$_2$O, 0.014% (w/v) MgCl$_2$.6H$_2$O, and 0.021% (w/v) NaHCO$_3$ with a hardness of 15° dH (deutsche Härte, German hardness). The substrate solution is heated to 70° C. and pH is adjusted to 8.5 at 50° C. using 0.1 N NaOH. The protease solution is prepared with 2% (w/v) anhydrous pentasodium tripolyphosphate in synthetic tap water, adjusted to pH 8.5 with hydrochloric acid.

To 600 µl of casein substrate solution 200 µl of enzyme solution is added. The mixture is incubated at 50° C. for 15 minutes. The reaction is terminated by the addition of 600 µl of 0.44 M trichloroacetic acid (TCA), 0.22 M sodium acetate in 3% (v/v) glacial acetic acid. After cooling on ice for 15 minutes the TCA-insoluble protein is removed by centrifugation, an aliquot of 900 µl is mixed with 300 µl of 2N NaOH and the absorbance of this mixture containing TCA-soluble peptides is recorded at 290 nm. Control values are produced by adding 600 µl of TCA solution to 600 µl of casein solution followed by 200 µl of enzyme solution.

A protease solution which produces under the conditions of this assay an absorbance change of 0.500 OD at 290 nm is declared to have an activity 10 HPE per ml.

Data for BLAP and BLAP mutant proteins are summarized below (Table 4).

B. Protease Assay With the Chromogenic Substrate AAPF-PNA

Protease samples were diluted with 50% (v/v) 1,2-propanediol in 100 mM Tris, adjusted with 2 N HCl to pH 8.6 at 25° C. ('Tris-propanediol buffer'), in which they were stable for at least 6 h at room temperature. A stock solution of 160 mM AAPF-pNA was prepared in dimethylsulfoxide dried over molecular sieve beads (Aldrich; 4 Å, 4–8 mesh) for at least 24 h prior to use.

Fixed point assays were performed at 25° C. with 1.6 mM AAPF-pNA in 100 mM Tris, adjusted with 2 N HCl to pH 8.6 at 25° C., in a total volume of 1.020 ml. The substrate was added to the assay buffer 1 minute prior to the assay initiation and the reaction was started by addition of enzyme at a final concentration of 20 ng to 1.3 µg of protein per ml (0.75 to 48.5 nM enzyme) depending on specific activity. Release of p-nitroanilide was monitored at 410 nm, and a molar extinction coefficient of 8,480 $M^{-1}cm^{-1}$ was used to calculate amount and concentration of product formed (DelMar, E. G., Largman, C., Brodrick, J. W., and Geokas, M. C. (1979) Anal Biochem. 99, 316–320).

Kinetic parameters were calculated from a velocity vs. substrate concentration plot constructed from initial rates measured once each at 12 different AAPF-pNA concentrations ranging from 0.16 to 3.2 mM. Data were fitted to a hyperbolic curve and proportionally weighted using the program ENZFITTER (Leatherbarrow, R. J. (1987) ENZFITTER. Biosoft, Cambridge, UK). A nominal molecular weight of 26.8 kDa was used in all calculations that required the interconversion of protein concentration and molarity of protease enzyme (Table 4).

TABLE 4

Kinetic Data of BLAP and BLAP Mutant Proteases

| Protease Label | Specific Activity (HPE · $mg^{-1}$) | $k_{cat}$ ($s^{-1}$) | $K_m$ (mM) | $k_{cat} \cdot K_m^{-1}$ ($s^{-1} \cdot mM^{-1}$) |
|---|---|---|---|---|
| BLAP | 4000 | 312 | 1.05 | 297 |
| M131 | 3670 | 153 | 0.98 | 156 |
| F11 | 3760 | 174 | 1.88 | 92 |
| F43 | 3780 | 171 | 1.73 | 99 |
| F44 | 3750 | 257 | 2.49 | 103 |
| F45 | 3710 | 208 | 3.05 | 68 |
| F46 | 3180 | 358 | 2.0 | 179 |
| F47 | 3610 | 249 | 2.0 | 124 |
| F49 | 4610 | 38 | 3.5 | 11 |
| F54 | 2510 | 7 | 5.5 | 1.3 |
| F55 | 3200 | 11 | 4.3 | 2.6 |

EXAMPLE 8

Protein Structure Verification

Mutations introduced into the BLAP were verified by DNA sequence analysis through the immediate vicinity of the point of mutation. However, spontaneous mutations outside the region of site-directed mutagenesis are known to occur and it was imperative to establish that the determined property of a mutant protease indeed resides with the amino acid sequence deduced from the nucleotide sequence. Therefore, a tryptic map of BLAP was produced (FIG. 9) which was verified by amino acid sequence analysis of the individual peaks and to which all mutant BLAP proteins were compared. Not only in peptides with ≦17 amino acid residues, but also in peptides 5T, 7T, and 10T (FIG. 9) with 48, 44, and 49 amino acid residues, a single (even conservative) substitution resulted in a significant change in retention time under the conditions of the separation.

Particularly close calls were resolved by co-digestion of equal quantities of the reference (BLAP) and the mutant protein.

An aliquot of up to 5 mg of protease from a stock solution was placed on ice in a 2.2-ml Eppendorf tube, then mixed with 1.0 ml of 0.15 N HCl and water (both chilled) to give a final concentration of 3.33 mg·$ml^{-1}$ protein and 0.1 N HCl in a total volume of 1.5 ml. After the mixture had been incubated for 30 minutes, protein was precipitated by the addition of 165 µl of chilled 50% (w/v) trichloroacetic acid (TCA). The precipitate was allowed to stand on ice for 5 minutes and then pelleted by centrifugation for 4 minutes at 13,000×$g_{max}$ (Eppendorf centrifuge). The pellet was washed once with 1 ml of 80% (v/v) acetone and briefly dried in vacuo.

All reagent solutions and water needed for the tryptic digest were passed through a 0.45 µm filter (Ultrafree-MC, Millipore Products) prior to use. The pellet of the denatured protein (5 mg; 185 nmol) was dissolved in 90 µl of 0.8 M ammonium bicarbonate, containing 8 M urea. This solution was slowly diluted with 360 µl of water and then passed by centrifugation through a 0.45 µm filter. Subsequent steps were carried out in 0.5-ml siliconized microtubes (Phenix Res. Products). An aliquot of 300 µl was mixed with 13 µl of 2.5 mg·$ml^{-1}$ trypsin in 1 mM HCl (mass ratio of BLAP:trypsin=100:1). For a control, 100 µl of the protein solution was mixed with 4.5 µl of 1 mM HCl. The remaining 50 µl aliquot of protein solution was mixed with 5 µl of 10% (v/v) trifluoroacetic acid (TFA) and used as control of the starting material. The two other solutions were incubated for 10 minutes at 37° C. The reactions were terminated by adding 30 µl and 10 µl of 10% (v/v) TFA to the digest and the control, respectively. The peptide mixture was separated by reverse-phase HPLC.

The HPLC equipment was from Waters and consisted of an autosampler (model 715 Ultra Wisp), a dual pump system (model 600E) and a diode array detector (model 990). Sampling and gradient formation was governed by Waters' software program '990⁺ Powerline'. Tryptic peptides were separated on a $C_{18}$ column (Vydac model 218TP54; 4.6×250 mm; 5 µ particle size; 300 Å pore size). In line with the separation column was a $C_{18}$ guard column (Vydac model 218FSK104, 10 µ particle size). Separation column and guard column were housed in a column heater set to 30±1° C. The solvent system used was: Solvent A=0.1% (v/v) TFA in water; Solvent B=0.08% (v/v) TFA in acetonitrile.

After sample loading the $C_{18}$ column was developed for 3 minutes with Solvent A followed by a gradient from 0 to 35% (v/v) of Solvent B in Solvent A in 70 minutes. At 70 minutes the gradient increased to 100% Solvent B in 15 minutes and then returned to 100% Solvent A in 15 minutes. Prior to the next injection, the column was equilibrated for at least 20 minutes with Solvent A.

Absorbance changes were recorded at 215 nm and at 280 nm. Quantities of peptides mixtures separated for analytical and preparative purposes ranged from 11 μg (0.4 nmol) to 500 μg (18 nmol) in a volume of 5 to 50 μl at concentrations from 2.2 to 10 mg·ml$^{-1}$.

For peptide sequencing the eluate was hand-fractionated according to absorbance changes observed on the attached recorder. Previous studies with β-mercaptoethanol showed that the delay time from the time of recording to the time of elution from the system was less than 2 seconds. Fractions were concentrated in vacuo in a Speed Vac Concentrator (Savant, Hicksville, N.Y.) to less than 100 μl and brought to 100 μl with aqueous TFA to achieve a final TFA concentration of 1%. Care was taken that during concentration the samples did not reach complete dryness.

EXAMPLE 9

Characterization of the Proteases by Tenside Stability

Stability of the protease mutants to tensides was tested with SDS as typical anionic detergent. Stability was tested in 50 mM sodium carbonate, pH 10.5 at 50° C., containing 1% (w/v) SDS. Protease proteins were incubated at a final protein concentration of 0.25 mg·ml$^{-1}$. Periodically, an aliquot was removed from the incubation mixture and diluted into Tris-propanediol buffer chilled on ice. Residual protease activity was determined by the AAPF-PNA assay at a substrate concentration of 1.1 mM. Stability is expressed as half-life ($t_{1/2}$) of activity determined from semilogarithmic plots of residual activity as function of time.

EXAMPLE 10

Wash Performance of the Protease Mutants

The wash performance was tested in a specially developed washing test using cotton swatches soiled with egg and soot (ER) and with blood, milk and soot (BMR). The washing tests were performed in an Atlas launderometer (type LP 2), equipped with stainless steel test vessels each containing a defined detergent composition plus the protease to be tested.

The pre-washed cotton was soiled with a defined amount of soil and air-dried for 6 days. The launderometer beakers were filled with 1 swatch of soiled and 3 swatches of unsoiled cotton. Ten metal balls (10 mm diameter) were added for mechanical treatment. The washing time was 30 minutes with a final temperature of 30° C. reached after 4 minutes of heating.

Laundry detergents for these tests were of typical composition for European usage (Jakobi, G. and Löhr, A. (1987) *Detergents and Textile Washing*, VCH, Weinheim, Germany). The concentrations of a delicate fabric detergent for easy-care and colored fabrics (5–15% (w/w) anionic surfactants, 1–5% (w/w) nonionic surfactants), a heavy duty compact detergent (8% (w/w) anionic surfactants, 6% (w/w) nonionic surfactants, with tetraacetylethylenediamine (TAED) and perborate bleach) and a super compact detergent concentrate (18% (w/w) anionic surfactants, 2.5% (w/w) nonionic surfactants, with TAED and perborate bleach) were 0.5 g, 0.5 g, and 0.4 g, respectively, in 100 ml of water at 16° dH (deutsche Härte, German hardness). The super compact detergent is an extruded detergent granulate, described by a number of patent applications (WO 91/02047, WO 91/13678, WO 93/02176, WO 93/15180, WO 94/01526). In all cases the pH was 10.4.

A protease was added to washing solutions on the basis of its enzymatic activity measured in HPE at a ratio of 0, 50, 100, 200, 300, 400, 500, 700 and 1000 HPE per gram of detergent.

Subsequent to washing, the fabric was rinsed with running tap water, air-dried and ironed. The enzymatic washing effect was determined by the change (ΔRem) of the remission (% Rem) at 440 nm (400–500 nm) measured on a Dr. Lange color difference measuring instrument (Micro Color).

ΔRem is the difference in remission after washing with added protease and the remission after washing without added protease. Results from the wash performance tests are presented in Tables 5 and 6.

The improvement in washing performance was determined by the ratio of wild type enzyme necessary to achieve a standard ΔRem, versus the amount of mutant enzyme to achieve an identical effect. Thus an improvement of 2 indicates that half of the mutant enzyme is needed to get the same effect as with the wild type enzyme.

TABLE 5

Washing Effect of BLAP and BLAP Mutant Proteins on Blood-Milk-Soot-Stains

| | Detergent | | |
| --- | --- | --- | --- |
| Enzyme | A[1] Improvement Ratio[2] | B Improvement Ratio | C Improvement Ratio |
| BLAP | 1 | 1 | 1 |
| M131 | 1 | 1 | 1 |
| F43 | 2.8 | 1.8 | 0.7 |
| F44 | 2.0 | 1.8 | <0.7 |
| F45 | 2.6 | 1.1 | <0.7 |
| F46 | 2.9 | 1.9 | 1 |
| F47 | 1.5 | 1.8 | 0.8 |
| F49 | 1.8 | 1 | 2.5 |

[1]Detergent A is a Heavy Duty Compact Detergent, Detergent B is a Heavy Duty Super Compact Detergent and Detergent C is a Delicate Fabric Detergent.
[2]For definition see text.

TABLE 6

Washing Effect of BLAP and BLAP Mutant Proteins on Egg-Soot-Stains

| | Detergent | |
| --- | --- | --- |
| Enzyme | Heavy Duty Compact Detergent Improvement Ratio[1] | Heavy Duty Super Compact Detergent Improvement Ratio |
| BLAP | 1 | 1 |
| M131 | 1 | 1 |
| F46 | 1.5 | 1 |
| F47 | 1 | 1 |
| F49 | 4.0 | 1.7 |

[1]For definition see text.

EXAMPLE 11

An enzymatic detergent composition is prepared by mixing about 30 wt % of a concentrated preparation of a subtilisin protease mutant comprising one or more of the following mutations: R99G, R99A, R99S, R99E, L211D, L211E, S154D and S154E, with about 5 wt % of cellulose, 5 wt % of saccharose, 20 wt % of wheat flour, 30 wt % of starch, 5 wt % of carboxymethylcellulose and 5% of polyethylene glycol (mw 20,000). The resulting mixture is granulated by extrusion granulation. After drying, the granulate has an activity of 70,000 to 250,000 HPE/g. The granulate is coated with polyethylene glycol (mw 6000) containing $TiO_2$. The granulated protease enzyme is then mixed with 100 g Heavy Duty Compact Detergent (Porsil supra) containing sodium perborate\TAED resulting in a standard protease activity of 1200 HPE/g.

EXAMPLE 12

An enzymatic detergent composition is prepared according to Example 11 except the protease is replaced by a mutated *Bacillus lentus* DSM 5483 alkaline protease comprising one or more of the following mutations: S3T, V4I, R99G, R99A, R99S, S154D, S154E, A188P, V193M, V199I, L211D and L211E.

EXAMPLE 13

A liquid enzymatic detergent composition is prepared by mixing together at room temperature about 13 wt % C10–C13 linear alkylbenzene-sulfonic acid, about 5 wt % alkylpolyglycoside(C12–C14), about 10 wt % of a C13 alcohol polyethoxylate having 7 EO units, about 6 wt % lauric acid, about 7 wt % of oleic acid, about 5 wt % triethanolamine, about 5 wt % propanediol 1,2, about 2 wt sodium hydroxide, about 1 wt % citric acid, about 7 wt % ethanol, about 1 wt % citric acid about 7 wt % ethanol, about 1-hydroxyethane-1,1-diphosphonic acid and the remainder being water.

The pH of the resulting solution is 8.1 (measured as a 10% aqueous solution). A sufficient amount of the subtilisin protease comprising one or more of the following mutations: R99G, R99A, R99S, R99E, L211D, L211E, S154D and S154E is added to yield a composition having about 0.5 wt % of liquid protease concentrate (1250 HPE/g).

EXAMPLE 14

A similar composition as described in example 13 is prepared except the protease is replaced by a mutated *Bacillus lentus* DSM 5483 alkaline protease comprising one or more of the following mutations: S3T, V4I, R99G, R99A, R99S, S154D, S154E, A188P, V193M, V199I, L211D and L211E.

What is claimed is:

1. A nucleic acid encoding a polypeptide comprising a protease M130 variant having at least two amino acid alterations which provide an increased negative charge relative to protease M130 in the domain of a substrate binding pocket within 7 Å of a bound substrate molecule.

2. A nucleic acid encoding a polypeptide according to claim 1 wherein the at least two amino acid alterations are amino acid substitutions at at least two positions selected from the group consisting of position 99, position 154, and position 211, of protease M 130.

3. A nucleic acid encoding a polypeptide according to claim 2 wherein the amino acid used for substitution at position 154 is selected from the group consisting of glutamic acid and aspartic acid.

4. A nucleic acid encoding a polypeptide according to claim 2 wherein the amino acid used for substitution at position 211 is selected from the group consisting of glutamic acid and aspartic acid.

5. A nucleic acid encoding a polypeptide according to claim 2 wherein the at least two amino acid alterations are substitutions made with one or more amino acid residues selected from the group consisting of glutamic acid, aspartic acid, glycine, alanine and serine.

6. A nucleic acid encoding a polypeptide according to claim 1 further comprising in the direction of transcription, a promoter, a ribosomal binding site, an initiation codon, and at least a portion of DNA encoding the sequence of *B. licheniformis* ATCC 53926 alkaline protease operably linked to additional nucleic acid including at least a portion of the pre sequence, the pro and mature sequence of the protease M130 variant, the additional nucleic acid operatively linked to and followed by the *B. licheniformis* ATCC 53926 transcription terminator.

7. A nucleic acid encoding a polypeptide comprising a protease M131 variant having at least two amino acid alterations which provide an increased negative charge relative to protease M131 in the domain of a substrate binding pocket within 7 Å of a bound substrate molecule.

8. A nucleic acid encoding a polypeptide according to claim 7 wherein the at least two amino acid alterations are amino acid substitutions in at least two positions selected from the group consisting of position 99, position 154, and position 211, of protease M131.

9. A nucleic acid encoding a polypeptide according to claim 8 wherein the amino acid used for substitution at position 154 is selected from the group consisting of glutamic acid and aspartic acid.

10. A nucleic acid encoding a polypeptide according to claim 8 wherein the amino acid used for substitution at position 211 is selected from the group consisting of glutamic acid and aspartic acid.

11. A nucleic acid encoding a polypeptide according to claim 8 comprising the sequence shown in SEQ ID No: 8.

12. A nucleic acid encoding a polypeptide according to claim 8 comprising the sequence shown in SEQ ID No: 9.

13. A nucleic acid encoding a polypeptide according to claim 7 further comprising in the direction of transcription, a promoter, a ribosomal binding site, and initiation codon, and at least a portion of DNA encoding the sequence of *B. licheniformis* ATCC 53926 alkaline protease operably linked to additional nucleic acid including a portion of the pre sequence, the pro and mature sequence of the protease M131 variant, the additional nucleic acid operatively linked to and followed by the *B. licheniformis* ATCC 53926 transcription terminator.

14. A nucleic acid encoding a polypeptide comprising a protease M131 variant having at least one amino acid alteration which provides an increased negative charge relative to protease M131 in the domain of a substrate binding pocket within 7 Å of a bound substrate molecule wherein position 99 is altered by substitution and the amino acid used for substitution at position 99 is selected from the group consisting of serine, glycine and alanine and said variant comprises the sequence shown in SEQ ID No.: 3.

15. A nucleic acid encoding a polypeptide comprising a protease M131 variant having at least one amino acid alteration which provides an increased negative charge relative protease M131 in the domain of a substrate binding pocket within 7 Å of a bound substrate molecule wherein position 99 is altered by substitution and the amino acid used for substitution at position 99 is selected from the group consisting of serine, glycine and alanine and said variant comprises the sequence shown in SEQ ID No.: 4.

16. A nucleic acid encoding a polypeptide comprising a protease M131 variant having at least one amino acid alteration which provides an increased negative charge relative to protease M131 in the domain of a substrate binding pocket within 7 Å of a bound substrate molecule wherein the protease M131 variant includes the sequence shown in SEQ ID No: 7, and wherein the protease M131 variant has improved wash performance relative to protease M131.

17. A nucleic acid encoding a polypeptide comprising a BLAP variant having at least two amino acid alterations which provide an increased negative charge relative to BLAP in the region of a substrate binding pocket within 7 Å of a bound substrate molecule.

18. A nucleic acid encoding a polypeptide according to claim 17 wherein the at least two amino acid alterations are amino acid substitutions at at least two positions selected from the group consisting of position 99, position 154, and position 211, of BLAP.

19. A nucleic acid encoding a polypeptide according to clime 18 wherein the amino acid used for substitution at position 154 is selected from the group consisting of glutamic acid and aspartic acid.

20. A nucleic acid encoding a polypeptide according to claim 18 wherein the amino acid used for substitution at position 211 is selected from the group consisting of glutamic acid and aspartic acid.

21. A nucleic acid encoding a polypeptide according to claim 17 further comprising in the direction of transcription, a promoter, a ribosomal binding site, an initiation codon, and at least a portion of DNA encoding the sequence of *B. licheniformis* ATCC 53926 alkaline protease operably linked to additional nucleic acid including a portion of the pre sequence, the pro and mature sequence of the BLAP variant, the additional nucleic acid operatively linked to and followed by the *B. licheniformis* ATCC 53926 transcription terminator.

22. A nucleic acid encoding a BLAP variant comprising at least two amino acid alterations which provide an increased negative charge relative to BLAP in the region of a substrate binding pocket within 7 Å of a bound substrate molecule wherein the BLAP variant has improved wash performance relative to BLAP.

23. The nucleic acid encoding a BLAP variant according to claim 22 wherein the at least two amino acid alterations are amino acid substitutions at at least two positions selected from the group consisting of position 99, position 154 and position 211 of BLAP.

24. The nucleic acid encoding a BLAP variant according to claim 23 wherein the amino acids used for substitution are selected from the group consisting of glutamic acid, aspartic acid, glycine, alanine and serine.

25. The nucleic acid encoding a BLAP variant according to claim 23 wherein the amino acid used for substitution at position 211 is selected from the group consisting of glutamic acid and aspartic acid.

26. The nucleic acid encoding a BLAP variant according to claim 23 wherein the amino acid used for substitution at position 154 is selected from the group consisting of glutamic acid and aspartic acid.

27. The nucleic acid encoding a BLAP variant according to claim 23 wherein the amino acid used for substitution at position 99 is selected from the group consisting of serine, glycine, and alanine.

28. The nucleic acid encoding a BLAP variant according to claim 23 wherein the BLAP variant is selected from the group consisting of BLAP M130 variant and BLAP M131 variant.

29. The nucleic acid encoding a BLAP variant according to claim 22 further comprising in the direction of transcription, a promoter, a ribosomal binding site, an initiation codon, and at least a portion of DNA encoding the sequence of *B. licheniformis* ATCC 53926 alkaline protease operably linked to additional nucleic acid including a portion of the pre sequence, the pro and mature sequence of the BLAP variant, the additional nucleic acid operatively linked to and followed by the *B. licheniformis* ATCC 53926 transcription terminator.

30. A replicable vector comprising a nucleic acid according to claim 22.

31. A host cell comprising a replicable vector according to claim 30.

32. A replicable vector comprising a nucleic acid selected from the group consisting of:
  (i) a nucleic acid encoding a protease M130 variant having at least two amino acid alterations which provide an increased negative charge relative to protease M130 in the region of a substrate binding pocket within 7 Å of a bound substrate molecule and
  (ii) a nucleic acid encoding a protease M131 variant having at least two amino acid alterations which provide an increased negative charge relative to protease M131 in the region of a substrate binding pocket within 7 Å of a bound substrate molecule.

33. The replicable vector according to claim 32 wherein the nucleic acid encoding a protease M130 variant provides an amino acid substitution at at least two positions selected from the group consisting of position 99, position 154, and position 211, of protease M130.

34. The replicable vector according to claim 32 wherein the nucleic acid encoding a protease M131 variant provides an amino acid substitution at at least two positions selected from the group consisting of position 99, position 154, and position 211, of protease M131.

35. The replicable vector according to claim 34 wherein the nucleic acid encoding a protease M131 variant is a sequence selected from the group consisting of those shown in SEQ ID No: 8 and SEQ ID No: 9.

36. A replicable vector comprising a nucleic acid selected from the group consisting of;
  (i) a nucleic acid encoding a protease M130 variant having the sequence shown in SEQ ID No: 1 wherein the protease M130 variant has improved wash performance relative to protease M130 and
  (ii) a nucleic acid encoding a protease M131 variant having a sequence selected from the group consisting of SEQ ID No: 3, SEQ ID No: 4, and SEQ ID No. 7 wherein the protease M131 variant has improved wash performance relative to protease M131.

37. A replicable vector comprising nucleic acid encoding a BLAP variant having at least two amino acid alterations which provide an increased negative charge relative to BLAP in the region of a substrate binding pocket within 7 Å of a bound substrate molecule.

38. The replicable vector according to claim 37 wherein the nucleic acid encoding a BLAP variant provides an amino acid substitution at a position selected from the group consisting of position 99, position 154, position 211 and combinations thereof, of BLAP.

39. The replicable vector according to claim 38 wherein one of the substitutions is at position 99 and the amino acid used for substitution at position 99 is selected from the group consisting of serine, glycine and alanine.

40. The replicable vector according to claim 38 wherein the amino acid used for substitution at position 154 is selected from the group consisting of glutamic acid and aspartic acid.

41. The replicable vector according to claim 38 wherein the amino acid used for substitution at position 211 is selected from the group consisting of glutamic acid and aspartic acid.

42. The replicable vector according to claim 32 wherein the vector is a plasmid.

43. The replicable vector according to claim 37 wherein the vector is plasmid.

44. The replicable vector according to claim 36 wherein the vector is plasmid.

45. A composition comprising a host cell transformed with the replicable vector of claim 32.

46. The composition according to claim 45 wherein the nucleic acid encoding a protease M130 variant provides an amino acid substitution at at least two positions selected from the group consisting of position 99, position 154, and position 211, of protease M130.

47. The composition according to claim 45 wherein the nucleic acid encoding a protease M131 variant provides an amino acid substitution at at least two positions selected from the group consisting of position 99, position 154, and position 211, of protease M131.

48. The composition according to claim 47 wherein the nucleic acid encoding a protease M131 variant is a sequence selected from the group consisting of those shown in SEQ ID No: 8 and SEQ ID No: 9.

49. The composition according to claim 45 wherein the host cell is Bacillus sp.

50. The composition according to claim 49 wherein Bacillus sp. is selected from the group consisting of *Bacillus licheniformis* and *Bacillus subtilis*.

51. A composition comprising a host cell transformed with the replicable vector of claim 37.

52. The composition according to claim 51 wherein the nucleic acid encoding a BLAP variant provides an amino acid substitution at at least a position selected from the group consisting of position 99, position 154, position 211 and combinations thereof, of BLAP.

53. The composition according to claim 52 wherein one of the substitutions is at position 99 and the amino acid used for substitution at position 99 is selected from the group consisting of serine, glycine and alanine.

54. The composition according to claim 52 wherein the amino acid used for substitution at position 154 is selected from the group consisting of glutamic acid and aspartic acid.

55. The composition according to claim 52 wherein the amino acid used for substitution at position 211 is selected from the group consisting of glutamic acid and aspartic acid.

56. The composition according to claim 51 wherein the host cell is Bacillus sp.

57. The composition according to claim 51 wherein Bacillus sp. is selected from the group consisting of *Bacillus licheniformis* and *Bacillus subtilis*.

58. A host cell comprising a replicable vector according to claim 36.

59. The composition according to claim 58 wherein the nucleic acid encoding a protease M130 variant is the sequence shown in SEQ ID No: 1.

60. The host cell according to claim 44 wherein the nucleic acid encoding a protease M131 variant has the sequence shown in SEQ ID No: 7.

61. The host cell according to claim 58 wherein the nucleic acid encoding a protease M131 variant has a sequence selected from the group consisting of those shown in SEQ ID No: 3 and SEQ ID No: 4.

62. The host cell according to claim 58 wherein the host cell is Bacillus sp.

63. The host cell according to claim 62 wherein the Bacillus sp. is selected from the group consisting of *Bacillus licheniformis* and *Bacillus subtilis*.

* * * * *

UNITED STATES PATENT AND TRADEMARK OFFICE
CERTIFICATE OF CORRECTION

PATENT NO. : 6,197,589 B1
DATED : March 6, 2001
INVENTOR(S) : Maurer et al.

It is certified that error appears in the above-identified patent and that said Letters Patent is hereby corrected as shown below:

Column 60,
Line 16, delete "clime", and insert therefor -- claim --.
Line 61, delete "claim 23", and insert therefor -- claim 22 --.

Column 61,
Line 37, after "of", delete ";", and insert therefor -- : --.

Column 62,
Lines 45, 47 and 62, delete "Bacillus sp.", and insert therefor -- *Bacillus sp.* --.
Line 54, delete "claim 44", and insert therefor -- claim 58 --.

Signed and Sealed this

Ninth Day of September, 2003

JAMES E. ROGAN
*Director of the United States Patent and Trademark Office*